(12) United States Patent
Stzepourginski et al.

(10) Patent No.: US 11,421,222 B2
(45) Date of Patent: Aug. 23, 2022

(54) BACTERIAL DELIVERY VEHICLES COMPRISING TRACER NUCLEIC ACID SEQUENCES

(71) Applicant: Eligo Bioscience, Paris (FR)

(72) Inventors: Igor Stzepourginski, Paris (FR); Daniel Garry, Paris (FR)

(73) Assignee: ELIGO BIOSCIENCE, Paris (FR)

( * ) Notice: Subject to any disclaimer, the term of this patent is extended or adjusted under 35 U.S.C. 154(b) by 0 days.

(21) Appl. No.: 16/905,656

(22) Filed: Jun. 18, 2020

(65) Prior Publication Data

US 2021/0002631 A1 Jan. 7, 2021

Related U.S. Application Data

(60) Provisional application No. 62/863,155, filed on Jun. 18, 2019.

(51) Int. Cl.
| | |
|---|---|
| *C12N 15/10* | (2006.01) |
| *C12N 7/00* | (2006.01) |
| *C12Q 1/70* | (2006.01) |
| *C40B 20/08* | (2006.01) |

(52) U.S. Cl.
CPC .......... *C12N 15/1065* (2013.01); *C12Q 1/70* (2013.01); *C12N 7/00* (2013.01); *C12Q 2600/136* (2013.01); *C12Q 2600/16* (2013.01); *C40B 20/08* (2013.01)

(58) Field of Classification Search
None
See application file for complete search history.

(56) References Cited

U.S. PATENT DOCUMENTS

2017/0029811 A1* 2/2017 Weiner ............... C12N 15/1037

FOREIGN PATENT DOCUMENTS

| WO | 2016061695 A1 | 4/2016 |
|---|---|---|
| WO | 2018126108 A1 | 7/2018 |
| WO | 2019243373 A1 | 12/2019 |

OTHER PUBLICATIONS

Mohammadi-Kambs et al., "Hamming Distance as a Concept in DNA Molecular Recognition," ACS Omega, 2017, vol. 2; pp. 1302-1308.
Kress et al., "DNA barcodes for ecology, evolution, and conservation," Cell Press, Trends in Ecology & Evolution vol. 30, Issue 1, Jan. 2015; pp. 25-35.
Espinosa et al., "Replication and Control of Cirular Bacterial Plasmids," Miciobiology and Molecular Biology Reviews, Jun. 1998; vol. 62, No. 2; pp. 434-464.
Krupovk et al., "Taxonomy of prokaryotic viruses: update from the ICTV bacterial and archaeal viruses subcommittee," Arch Virol (2016), vol. 161; pp. 1095-1099.
International Search Report and Written Opinion of the International Searching Authority dated Oct. 5, 2020, corresponding to counterpart International Application No. PCT/EP2020/067014; 16 total pages.
Lyons et al., "Large-scale DNA Barcode Library Generation for Biomolecule Identification in High-throughput Screens," Scientific Reports, 2017, vol. 7, 1399; pp. 1-8.

* cited by examiner

*Primary Examiner* — Nicole Kinsey White
(74) *Attorney, Agent, or Firm* — Carter, DeLuca & Farrell LLP

(57) ABSTRACT

The present disclosure relates generally to genetically tagged bacterial delivery vehicles comprising unique tracer nucleic acid sequences (herein referred to as "tracers") for use in detecting and/or quantitating the presence of two or more different said bacterial delivery vehicles within a mixture of vehicles. The present disclosure relates to methods wherein the bacterial delivery vehicles are detected through, for example, performance of multiple cycles of amplification using primers that bind to sequences within the unique tracer. Such methods can be advantageously used in quality control to detect and quantitate mixtures of bacterial delivery vehicles within a pharmaceutical composition.

25 Claims, 5 Drawing Sheets

Specification includes a Sequence Listing.

| Amino acid position: | 40 | 41 | 42 | 43 | 44 | 45 | 46 | 47 | 48 | 49 |
|---|---|---|---|---|---|---|---|---|---|---|
| Amino acid: | A | R | V | G | Y | I | E | L | D | L |
| Possible codons: | GCT | CGT | GTT | GGT | TAT | ATT | GAA | CTT | GAT | CTT |
| | GCC | CGC | GTC | GGC | TAC | ATC | GAC | CTC | GAC | CTC |
| | GCA | CGA | GTA | GGA | | ATA | | CTA | | CTA |
| | GCG | CGG | GTG | GGG | | | | CTG | | CTG |
| | | AGA | | | | | | TTA | | TTA |
| | | AGG | | | | | | TTG | | TTG |
Figure 4
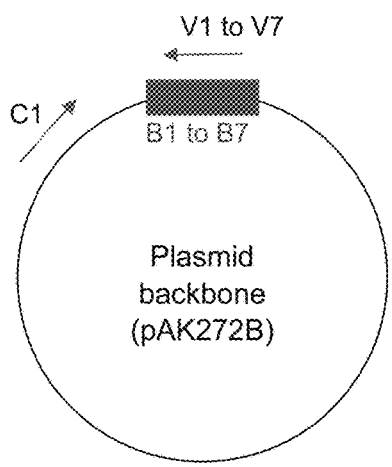
Figure 5
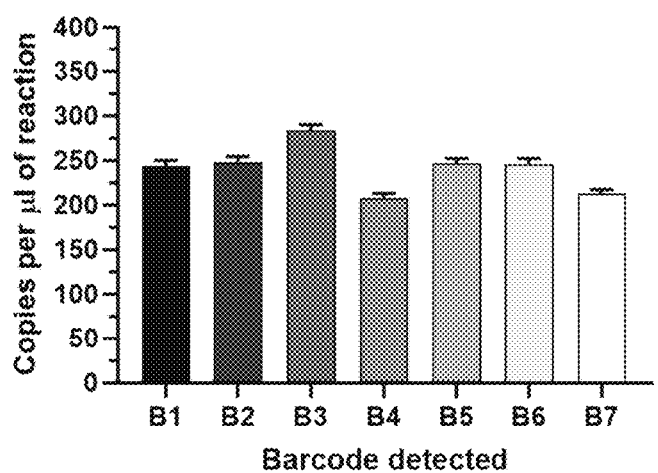
Figure 6

BACTERIAL DELIVERY VEHICLES COMPRISING TRACER NUCLEIC ACID SEQUENCES

CROSS-REFERENCE TO RELATED APPLICATION

This application claims benefit and priority to U.S. Provisional Application No. 62/863,155, filed Jun. 18, 2019, which is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "2643-9_ST25.txt" created on Jul. 7, 2020 and is 21,938 bytes in size. The sequence listing contained in this .txt file is part of the specification and is hereby incorporated by reference herein in its entirety.

TECHNICAL FIELD

The present disclosure relates generally to genetically tagged bacterial delivery vehicles comprising unique tracer nucleic acid sequences (herein referred to as "tracers") for use in detecting and/or quantitating the presence of two or more different said bacterial delivery vehicles within a mixture of vehicles. The present disclosure relates to methods wherein the bacterial delivery vehicles are detected through, for example, performance of multiple cycles of amplification using primers that bind to sequences within the unique tracer. Such methods can be advantageously used in quality control to detect and quantitate mixtures of bacterial delivery vehicles within a pharmaceutical composition.

BACKGROUND

Bacterial delivery vehicles, such as packaged phagemids, are bacteriophage derived particles composed of a DNA nucleic acid payload of interest packaged in a bacteriophage-derived capsid. The capsid being the major host range determinant, bacterial delivery vehicles are subject to similar host range limitations as bacteriophages, such that different bacterial delivery vehicles with complementary host ranges may be combined in a multivalent final drug product (a drug product with multiple target cell specificity) to achieve clinical efficacy. Accordingly, approaches using bacteriophage based bacterial delivery vehicles, for use as anti-microbials, may rely on cocktail formulations, where multiple phages with different host ranges are combined and administered as a mixture to a subject to maximize the clinical efficacy through targeting the maximal number of clinically relevant bacterial strains. In such instances, the different bacterial delivery vehicles of the final composition mixture have different capsids with varied host range and/or binding specificities while containing the same DNA or a different DNA (see FIG. 1).

From a regulatory standpoint, it is necessary to characterize the composition of a drug product before its administration to a subject. Notably, for drug products composed of mixtures of different drug substances, the presence and quantity of each drug substance in the final product must be confirmed. For example, the presence and quantity of each bacterial delivery vehicle within a pharmaceutical composition for use in treatment of a subject must be assessed in the final product and compliant with the specifications set for the drug. Accordingly, methods are needed to detect the presence and quantity of different bacterial delivery vehicles within a pharmaceutical composition for regulatory purposes.

SUMMARY

The present disclosure relates generally to methods for genetically tagging bacterial delivery vehicles for use in detecting the presence of two or more different (e.g. dissimilar in structure) bacterial delivery vehicles (herein referred to as a "multivalent mixture of bacterial delivery vehicles") within a sample. Each of the different bacterial delivery vehicles may be dissimilar, for example, through their distinct bacterial cell binding capability and/or their distinct host range and/or through inclusion of a different nucleic acid payload within said vehicle. More specifically, the present disclosure relates to methods wherein the bacterial delivery vehicles to be detected comprise a desired nucleic acid payload which additionally contains a unique tracer that can be detected through, for example, performance of cycles of amplification. Such methods can be advantageously used in quality control of pharmaceutical compositions comprising a multivalent bacterial delivery vehicle mixture.

In one aspect, bacterial delivery vehicles are provided wherein the bacterial delivery vehicle are engineered to bind to a target cell, such as a bacterial cell, and comprises a nucleic acid payload having a unique tracer embedded within the nucleic acid payload. In another aspect, a multivalent mixture of bacterial delivery vehicles is provided comprising two or more different bacterial delivery vehicles, wherein each bacterial delivery vehicle comprises a nucleic acid payload having a unique tracer nucleic acid sequence.

In one embodiment, each of the different bacterial delivery vehicles in a multivalent mixture comprises an identical nucleic acid payload, with the exception of having a unique tracer, associated with the identical payload. In another embodiment, each of the different bacterial delivery vehicles in a multivalent mixture comprises a different nucleic acid payload with a unique tracer associated with each of the different payloads. Linking of a unique tracer to a packaged nucleic acid payload allows one to identify and quantitate the associated bacterial delivery vehicle (herein referred to as "cognate bacterial delivery vehicle") into which the tagged DNA nucleic acid payload is packaged.

In some embodiments, the tracer comprises no more than 20 nucleotides homology stretch with the DNA of the bacterial production strain and/or the DNA of the target bacterial cell.

In an embodiment, the tracer comprises a barcode. In particular, the tracer may comprise a constant region and a barcode. In particular, the tracer may comprise a barcode flanked on each side by a constant region. The barcode and/or the constant region may be between 25 and 50 nucleic acids long.

The tracer may be embedded in a non-coding region or in a coding region. In embodiments wherein the tracer is embedded in a coding region, the tracer may comprise altered codon usage while encoding a protein with an unaltered amino acid sequence.

In some embodiments, bacterial delivery vehicles contained in the multivalent mixture are bacteriophage derived scaffolds.

Methods are provided for detecting and/or quantitating bacterial delivery vehicles in a multivalent mixture of bacterial delivery vehicles through detection of the unique tracer that correlates with the presence of a specific bacterial delivery vehicle. Said method comprises the step of detecting and, optionally, quantitating each of the bacterial delivery vehicles within a multivalent mixture of bacterial delivery vehicles through performance of cycles of amplification using primers that bind to nucleic acid sequences within the tracer sequence. Alternatively or additionally, the method may comprise the step of detecting and, optionally, quantitating in total the bacterial delivery vehicles within a multivalent mixture of bacterial delivery vehicles through performance of cycles of amplification using primers that bind to nucleic acid sequences within the tracer sequence. Such amplification methods include, for example, PCR, qPCR, ddPCR, LCR, FISH or NGS.

Additionally, methods are provided for detecting and tracking bacterial delivery vehicles following administration of a multivalent mixture of bacterial delivery vehicles to a subject wherein each bacterial delivery vehicle comprises a nucleic acid payload having a unique tracer. The method comprises the step of detecting and quantitating each of the different bacterial delivery vehicles within a subject derived sample through, for example, performance of cycles of amplification using primers that bind to nucleic acid sequences within the tracer. Amplification of the specific tracer sequences is then correlated with the presence of a specific bacterial delivery vehicle within the subject sample. Alternatively or additionally, the method may comprise the step of detecting and, optionally, quantitating in total the bacterial delivery vehicles within a sample derived from said subject, through performance of multiple cycles of amplification using primers that bind to the unique tracer nucleic acid sequence. Such amplification methods include, for example, PCR, qPCR, ddPCR or NGS.

In the methods provided herein, the unique tracer may have a constant region to which primers can bind for initiation of an amplification reaction, and thus the method may comprise detecting and, optionally, quantitating each bacterial delivery vehicle through amplification of the tracer using primers that bind within the constant region of the tracer sequence. Optionally, the unique tracer may further comprise variable sequences to which primers can bind for amplification and the method may further comprise a distinct amplification reaction or a second amplification reaction which uses primer binding to the variable sequences for an amplification method.

The unique tracer may comprise a variable region to which primers can bind for amplification, and thus the method may comprise detecting and, optionally, quantitating each bacterial delivery vehicle through amplification of the tracer using primers that bind within the variable region of the tracer sequence.

In the methods provided herein, each bacterial delivery vehicle may comprise a nucleic acid payload with an identical sequence with the exception of the tracer. Alternatively, each bacterial delivery vehicle may comprise a nucleic acid payload with different sequence and a different tracer associated with each different payload.

In a non-limiting embodiment, the tracer comprises no more than 20 nucleotides homology stretch with the DNA of the bacterial production strain and/or the DNA of the target bacterial cell.

In the methods provided herein, the tracer may comprise a barcode. In particular, the tracer may comprise a constant region and a barcode and more particularly a barcode flanked on each side by a constant region. In an embodiment, the barcode and/or the constant region are between 25 and 50 nucleic acids long.

In the methods provided herein, the tracer may be embedded in a non-coding region or in a coding region. In embodiments wherein the tracer is embedded in a coding region, the tracer may comprise altered codon usage while encoding a protein with an unaltered amino acid.

The present disclosure also provides a bacterial delivery vehicle as defined above, i.e. a bacterial delivery vehicle comprising a nucleic acid payload having a tracer nucleic acid sequence, as well as a pharmaceutical composition comprising a multivalent mixture of the invention.

The present disclosure also relates to a bacterial delivery vehicle or a pharmaceutical composition as described herein, for use in the treatment of a disease or disorder caused by bacteria. In an embodiment, the disease or disorder caused by bacteria is selected from the group consisting of infections caused by bacteria, metabolic disorders such as obesity and diabetes, and pathologies involving bacteria of the human microbiome.

BRIEF DESCRIPTION OF FIGURES

In order to better understand the subject matter that is disclosed herein and to exemplify how it may be carried out in practice, embodiments will now be described, by way of non-limiting example, with reference to the accompanying drawings. With specific reference to the drawings, it is stressed that the particulars shown are by way of example and for purposes of illustrative discussion of embodiments of the invention.

FIG. 4 (SEQ ID NO: 19) depicts representation of codon possibilities for the 10 amino acid segment AA40-49 in the TEM-1 beta-lactamase example.

FIG. 5 represents a schematic of plasmid backbone pAK272B, location of the barcode region and corresponding primers.

FIG. 6 represents number of each plasmid copies detected per µl from a mixture of different plasmids comprising each a different barcode.

DETAILED DESCRIPTION

Figure 1:
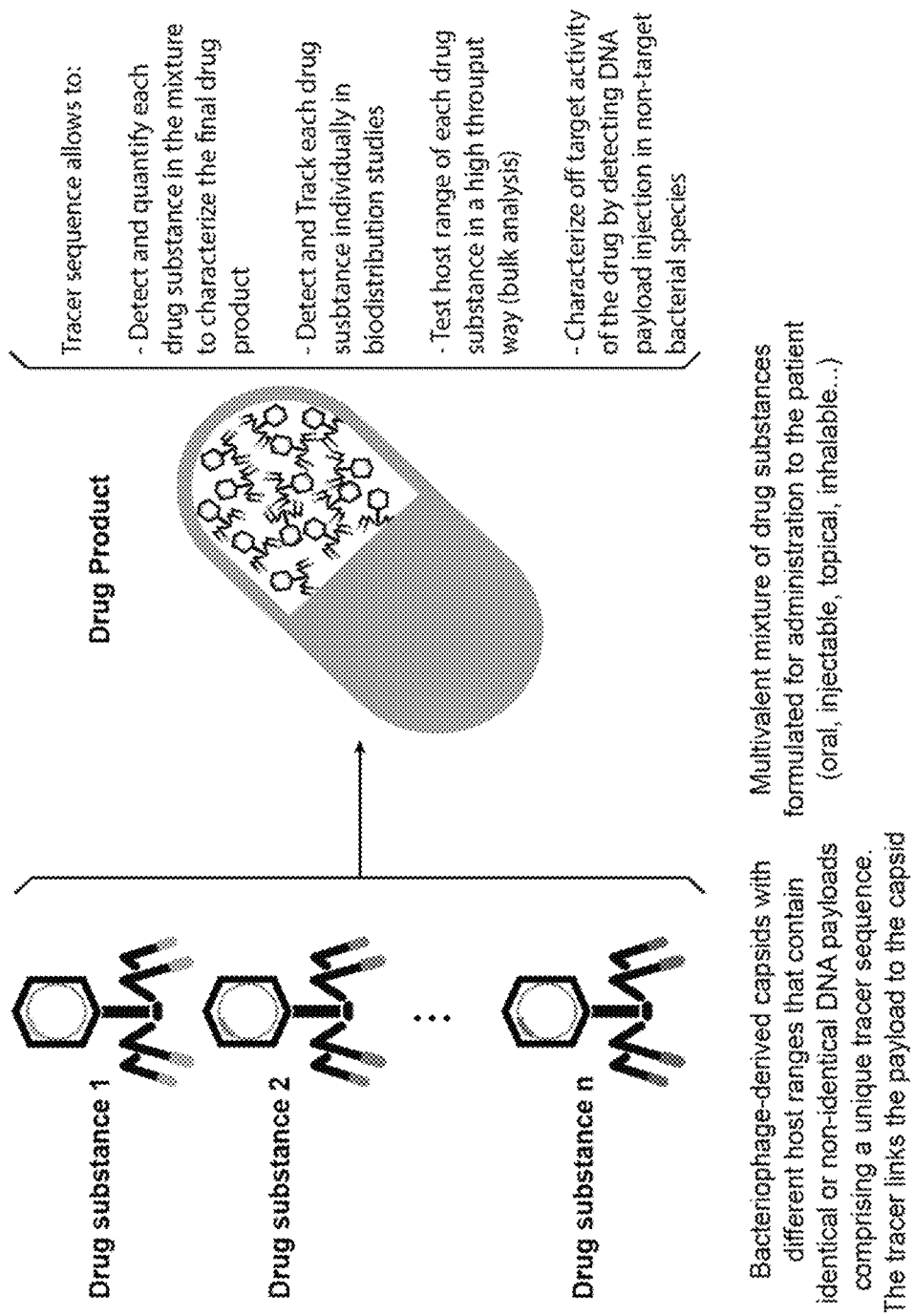
FIG. 1 demonstrates advantages of a mixture of phagemid particles containing unique DNA tracers in their DNA nucleic acid payload in the context of a drug application.

The present disclosure relates generally to methods for genetically tagging bacterial delivery vehicles, with desired structural features, for use in detecting the presence of two or more different bacterial delivery vehicles within a multivalent mixture of delivery vehicles. More specifically, the present disclosure relates to methods wherein the bacterial delivery vehicles to be detected comprise a desired nucleic acid nucleic acid payload of interest which additionally contains unique tracer nucleotide sequences that can be detected through performance of cycles of amplification.

In one aspect, a bacterial delivery vehicle is provided wherein the bacterial delivery vehicle has desired structural features, for example, specific target cell binding and/or host range, and comprises a nucleic acid payload having an embedded unique tracer nucleic acid sequence. In another aspect, a multivalent mixture of bacterial delivery vehicles is provided comprising two or more different bacterial delivery vehicles, wherein each bacterial delivery vehicle comprises a nucleic acid nucleic acid payload having a unique tracer nucleic acid sequence.

The bacterial delivery vehicles provided herein enable transfer of a nucleic acid payload, encoding a protein or nucleic acid of interest, into a desired target bacterial host cell. The bacteria targeted by bacterial delivery vehicles can be any bacteria present in a mammal organism. It can be any commensal, symbiotic or pathogenic bacteria of the microbiota or microbiome. Microbiota may comprise a variety of bacterial species, any of which may be targeted in accordance with the present disclosure. In some embodiments, the genus and/or species of targeted bacterial cells may depend on the type of bacteriophages being used for preparing the bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells. In a preferred embodiment, the target bacterial host cell is a cell of a microbiome. In a more preferred embodiment, the target bacterial host cell is a cell of the skin microbiome, the gut microbiome, the lung microbiome, the mouth microbiome.

As used herein, the term "delivery vehicle" refers to any means that allows the transfer of a nucleic acid payload into a bacterium. There are several types of delivery vehicles encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation). Any combination of delivery vehicles is also encompassed by the present invention. The delivery vehicle can refer to a bacteriophage derived scaffold and can be obtained from a natural, evolved or engineered capsid. In some embodiments, the delivery vehicle is the nucleic acid payload as bacteria are naturally competent to take up a nucleic acid payload from the environment on their own. In some embodiments, bacterial delivery vehicles are bacteriophage derived particles composed of a DNA nucleic acid payload of interest packaged in a bacteriophage-derived capsid.

The bacteriophage derived particles may be prepared from bacterial viruses. The bacterial viruses are chosen in order to be able to introduce the nucleic acid payload into the targeted bacteria.

Bacterial viruses are, for example, bacteriophages. Bacteriophage are obligate intracellular parasites that multiply inside bacteria by co-opting some or all of the host biosynthetic machinery. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

Optionally, the bacteriophage is selected from the Order Caudovirales consisting of, based on the taxonomy of Krupovic et al, Arch Virol, 2015:

family Myoviridae (such as, without limitation, genus Cp220virus, Cp8virus, Ea214virus, Felixolvirus, Mooglevirus, Suspvirus, Hplvirus, P2virus, Kayvirus, P100virus, Silviavirus, Spo1virus, Tsarbombavirus, Twortvirus, Cc31virus, Jd18virus, Js98virus, Kpl5virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, Ml2virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus), family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, T12011virus, Bcep22virus, Bpp1virus, Cba41virus, Dfl12virus, Ea92virus, Epsilonl5virus, F116virus, G7cvirus, Jwalphavirus, Kfl1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus), family Siphoviridae (such as, without limitation, genus Camvirus, Likavirus, R4virus, Acadianvirus, Coopervirus, Pglvirus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, T1svirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjwlvirus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1 virus, Phic31virus, Phicbkvirus, Phietavirus, Phifelvirus, Phijl1virus, Pis4avirus, Psavirus, Psimunavirus, Rdj1virus, Rer2virus, Sap6virus, Send513virus, Septima3virus, Seuratvirus, Sextaecvirus, Sfi11virus, Sfi21dtivirus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus), and family Ackermannviridae (such as, without limitation, genus Ag3virus, Limestonevirus, Cbal20virus and Vi1virus).

Optionally, the bacteriophage is not part of the Order Caudovirales but part of families with Unassigned order such as, without limitation, family Tectiviridae (such as genus *Alphatectivirus, Betatectivirus*), family Corticoviridae (such as genus *Corticovirus*), family Inoviridae (such as genus *Fibrovirus, Habenivirus, Inovirus, Lineavirus, Plectrovirus, Saetivirus, Vespertiliovirus*), family Cystoviridae (such as genus *Cystovirus*), family Leviviridae (such as genus *Allolevivirus, Levivirus*), family Microviridae (such as genus *Alpha3microvirus, G4microvirus, Phix174microvirus, Bdellomicrovirus, Chlamydiamicrovirus, Spiromicrovirus*) and family Plasmaviridae (such as genus *Plasmavirus*).

Optionally, the bacteriophage is targeting Archea and is not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Col1, Cor1, CP-53, CS-I, CSi, D, D, D, D5, ent1, FP8, FP9, FSi, FS2, FS3, FS5, FS8, FS9, G, GH8, GT8, GV-I, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-I, mor2, MP-7, MP1O, MP12, MP14, MP15, Neo1, N° 2, N5, N6P, PBC1, PBLA, PBP1, P2, S-a, SF2, SF6, Sha1, Si11, SP02, (syn=ΦSPP1), SPβ, STI, STi, SU-I1, t, TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tg13, Tg15, Tg21, Tin1, Tin7, Ting, Tin13, Tm3, Toc1, Tog1, tol1, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, p11, φmed-2, φT, φμ-4, φ3T, φ75, φ105, (syn=Φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), ale1, AR1, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, dar1, den1, DP-7, ent1, FoSi, FoS2, FS4, FS6, FS7, G, gal1, gamma, GE1, GF-2, GSi, GT-I, GT-2, GT-3, GT-4, GT-5, GT-6, GT-7, GV-6, g15, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMB1, PMB12, PMJ1, S, SPO1, SP3, SP5, SP6, SP7, SP8, SP9, SP1O, SP-15, SP50, (syn=SP-50), SP82, SST, sub1, SW, Tg8, Tg12, Tg13, Tg14, thu1, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (B. megateriwn), 4 (*B. sphaericus*), AR13, BPP-IO, BS32, BS107, B1, B2, GA-I, GP-IO, GV-3, GV-5, g8, MP20, MP27, MP49, Nf, PP5, PP6, SF5, Tg18, TP-I, Versailles, φ15, φ29, 1-97, 837/IV, mi-*Bacillus* (1), Bat1O, BSL1O, BSLI 1, BS6, BSI 1, BS16, BS23, BS1O1, BS102, g18, mor1, PBL1, SN45, thu2, thu3, TmI, Tm2, TP-20, TP21, TP52, type F, type G, type IV, HN-BacMus (3), BLE, (syn=θc), BS2, BS4, BS5, BS7, B10, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and μ.

Bacteria of the genus *Bacteroides* can be infected by the following phages: crAss-phage, ad 12, Baf-44, Baf-48B, Baf-64, Bf-I, Bf-52, B40-8, F1, β1, φA1, φBrO1, φBrO2, 11, 67.1, 67.3, 68.1, mt-*Bacteroides* (3), Bf42, Bf71, HN-*Bdellovibrio* (1) and BF-41.

Bacteria of the genus *Bordetella* can be infected by the following phages: 134 and NN-*Bordetella* (3).

Bacteria of the genus *Borrellia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=F01), (syn=FQ1), D, FP2, (syn=FP2), (syn=FD2), Fz, (syn=Fz75/13), (syn=Firenze 75/13), (syn=Fi), Fi, (syn=F1), Fim, (syn=FIm), (syn=Fim), FiU, (syn=F111), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=F1O), 371/XXIX, (syn=371), (syn=Fn), (syn=Fl1) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chp1.

Bacteria of the genus *Clostridium* can be infected by the following phages: CAK1, CA5, Cal, CEβ, (syn=1C), CEγ, C1dl, c-n71, c-203 Tox-, DEβ, (syn=ID), (syn=1Dt0X+), HM3, KM1, KT, Ms, NA1, (syn=Naltox+), PA135Oe, Pfó, PL73, PL78, PL81, P1, P50, P5771, P19402, 1CtOX+, 2CtOX\ 2D3 (syn=2Dt0X+), 3C, (syn=3Ct0x+), 4C, (syn=4CtOX+), 56, III-1, NN-*Clostridium* (61), NB1t0X+, α1, CA1, HMT, HM2, PF15 P-23, P-46, Q-05, Q-oe, Q-16, Q-21, Q-26, Q-40, Q-46, S111, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, α2, 41, 112ZS23, 214/S23, 233/Ai, 234/S23, 235/S23, II-1, 11-2, 11-3, NN-*Clostridium* (12), CA1, F1, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CG5), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γ19, δ, (syn=δ'ox+), p, (syn=ptoχ-), Φ9, φ984, w, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phages: DF78, F1, F2, 1, 2, 4, 14, 41, 867, D1, SB24, 2BV, 182, 225, C2, C2F, E3, E62, DS96, H24, M35, P3, P9, SB1O1, S2, 2BII, 5, 182a, 705, 873, 881, 940, 1051, 1057, 21096C, NN-*Enterococcus* (1), PE1, F1, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, E1, E24, E41, FI-2, FI-4, FI-5, HI8A, Ffl8B, i, MM, Mu, (syn=mu), (syn=MuI), (syn=Mu-I), (syn=MU-I), (syn=MuI), (syn=μ), 025, PhI-5, Pk, PSP3, P1, P1D, P2, P4 (defective), S1, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FI1, FI3, H, H1, H3, H8, K3, M, N, ND-2, ND-3, ND4, ND-5, ND6, ND-7, Ox-I (syn=OX1), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, PhI-I, RB42, RB43, RB49, RB69, S, SaI-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, al, 1, IA, 3, (syn=Ac3), 3A, 3T+, (syn=3), (syn=M1), 5φ, (syn=φ5), 9266Q, CFO103, HK620, J, K, K1F, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, (syn=(φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, (syn=ΦHK97), HK139, HK253, HK256, K7, ND-I, no.D, PA-2, q, S2, T1, (syn=α), (syn=P28), (syn=T-I), (syn=Tx), T3C, T5, (syn=T-5), (syn=T5), UC-I, w, (34, γ2, λ, (syn=lambda), (syn=Φλ, ΦD326, φγ, Φ06, Φ7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J, 933H, 0157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phages: NN-*Fusobacterium* (2), fv83-554/3, fv88-531/2, 227, fv2377, fv2527 and fv8501.

Bacteria of the genus *Haemophilus* are infected by the following phages: HP1, S2 and N3.

Bacteria of the genus *Helicobacter* are infected by the following phages: HP1 and ^^-*Helicobacter* (1).

Bacteria of the genus *Klebsiella* are infected by the following phages: AIO-2, KI4B, K16B, K19, (syn=K19), K114, K115, K121, K128, K129, KI32, K133, K135, K1106B, K1171B, K1181B, K1832B, AIO-I, AO-I, AO-2, AO-3, FC3-10, K, K11, (syn=KI1), K12, (syn=K12), K13, (syn=K13), (syn=K170/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, KIi65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=KI1 81), (syn=K1181B), K1765/!, (syn=K1765/1), K1842B, (syn=K1832B), K1937B, (syn=K1937B), L1, φ28, 7, 231, 483, 490, 632 and 864/100.

Bacteria of the genus Lepitospira are infected by the following phages: LE1, LE3, LE4 and ~NN-*Leptospira* (1).

Bacteria of the genus *Listeria* are infected by the following phages: A511, 01761, 4211, 4286, (syn=B054), A005, A006, A020, A500, A502, A511, A1 18, A620, A640, B012, B021, B024, B025, B035, B051, B053, B054, B055, B056, B101, BI1O, B545, B604, B653, C707, D441, HSO47, H1OG, H8/73, H19, H21, H43, H46, H107, H108, HI 1O, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/ 11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-Lisferia (15).

Bacteria of the genus *Morganella* are infected by the following phage: 47.

Bacteria of the genus *Mycobacterium* are infected by the following phages: 13, AG1, ALi, ATCC 11759, A2, B.C3, BG2, BK1, BK5, *butyricum*, B-I, B5, B7, B30, B35, Clark, C1, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI1, Mx4, MyF3P/59a, *phlei*, (syn=*phlei* 1), *phlei* 4, Polonus II, rabinovitschi, *smegmatis*, TM4, TM9, TM1O, TM20, Y7, Y1O, φ630, IB, IF, IH, 1/1, 67, 106, 1430, B1, (syn=Bol), B24, D, D29, F—K, F—S, HP, Polonus I, Roy, R1, (syn=R1-Myb), (syn=Ri), 11, 31, 40, 50, 103a, 103b, 128, 3111-D, 3215-D and NN-*Mycobacterium* (1).

Bacteria of the genus *Neisseria* are infected by the following phages: Group I, group II and NP1.

Bacteria of the genus *Nocardia* are infected by the following phages: MNP8, NJ-L, NS-8, N5 and TtiN-*Nocardia*.

Bacteria of the genus *Proteus* are infected by the following phages: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI 1, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phages: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phages: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PB1), pfl6, PMN17, PP1, PP8, Psal, PsP1, PsP2, PsP3, PsP4, PsP5, PS3, PS17, PTB80, PX4, PX7, PYO1, PYO2, PYO5, PYO6, PYO9, PYO1O, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, F1 16, HF, H90, K5, K6, K104, K109, K166, K267, N4, N5, 06N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, PX1O, PX12, PX14, PYO70, PYO71, R, SH6, SH133, tf, Ya5, Ya7, φBS, ΦKf77, φ-MC, ΦmnF82, φPLS27, φPLS743, 0-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F10, g, gd, ge, g Hw12, Jb 19, KF1, L°, OXN-32P, 06N-52P, PCH-I, PC13-1, PC35-1, PH2, PH51, PH93, PH132, PMW, PM13, PM57, PM61, PM62, PM63, PM69, PM105, PM113, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC1 1, φC11-1, φC13, φC15, φMO, φX, φO4, φ11, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G101, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, φ03, φO6 and 1214.

Bacteria of the genus *Rickettsia* are infected by the following phage: NN-*Rickettsia*.

Bacteria of the genus *Salmonella* are infected by the following phages: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, P10, Sab3, Sab5, San1S, San17, SI, Taunton, ViI, (syn=ViI), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22al, P22-4, P22-7, P22-11, SNT-I, SNT-2, SP6, Villi, ViIV, ViV, ViVI, ViVII, Worksop, Sj5, ε34, 1,37, 1(40), (syn=φ1[40]), 1,422, 2, 2.5, 3b, 4, 5, 6,14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, G173, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, VIII, φ1, 1, 2, 3a, 3al, 1010, Ym-*Salmonella* (1), N-4, SasL6 and 27.

Bacteria of the genus *Serratia* are infected by the following phages: A2P, PS20, SMB3, SMP, SMP5, SM2, V40, V56, ic, ΦCP-3, ΦCP-6, 3M, 10/1a, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCW1, ΦCP6-1, ΦCP6-2, ΦCP6-5, 3T, 5, 8, 9F, 10/1, 20E, 32/6, 34B, 34CT, 34P, 37, 41, 56, 56D, 56P, 60P, 61/6, 74/6, 76/4, 101/8900, 226, 227, 228, 229F, 286, 289, 290F, 512, 764a, 2847/10, 2847/10a, L.359 and SMB1.

Bacteria of the genus *Shigella* are infected by the following phages: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), SHvi, (syn=HVI), SHVvm, (syn=HVIII), SKy66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVHIA, (syn=SvmA), (syn=VIIIA), STvi, STK, STx1, STxn, S66, W2, (syn=D2c), (syn=D20), φ1, φIVb 3-SO-R, 8368-SO-R, F7, (syn=FS7), (syn=K29), F10, (syn=FS10), (syn=K31), I1, (syn=alfa), (syn=FSa), (syn=K18), (syn=α), 12, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=F1), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BI1, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI1, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=Si), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STff1, STrv, STVi, STvπ, S70, 5206, U2-S0-S, 3210-SO-S, 3859-SO-S, 4020-SO-S, φ3, φ5, φ7, φ8, φ9, φ1O, φ1 1, φ13, φ14, φ18, SHm, (syn=Hai), SHri, (syn=HXt) and SKxI, (syn=KXI), (syn=Sri), (syn=SsXI), (syn=XI).

Bacteria of the genus *Staphylococcus* are infected by the following phages: A, EW, K, Ph5, Ph9, PhIO, Ph13, P1, P2, P3, P4, P8, P9, P10, RG, SB-i, (syn=Sb-I), S3K, Twort, ΦSK311, φ812, 06, 40, 58, 119, 130, 131, 200, 1623, STC1, (syn=stc1), STC2, (syn=stc2), 44AHJD, 68, AC1, AC2, A6"C", A9"C", b581, CA-I, CA-2, CA-3, CA-4, CA-5, DI 1, L39x35, L54a, M42, N1, N2, N3, N4, N5, N7, N8, N10, Ni 1, N12, N13, N14, N16, Ph6, Ph12, Ph14, UC-18, U4, U15, S1, S2, S3, S4, S5, X2, Z1, φB5-2, φD, ω, 11, (syn=φ11), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A10, A13, b594n, D, HK2, N9, N15, P52, P87, 51, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phages: EJ-I, NN-Streptococais (1), a, C1, FL0Ths, H39, Cp-I, Cp-5, Cp-7, Cp-9, Cp-I0, AT298, A5, alO/J1, alO/J2, alO/J5, alO/J9, A25, BTI 1, b6, CA1, c20-1, c20-2, DP-I, Dp-4, DT1, ET42, e10, FA101, FETHs, Fκ, FKKIOI, FKLIO, FKP74, FKH, FLOThs, FyIO1, f1, F10, F20140/76, g, GT-234, HB3, (syn=HB-3), HB-623, HB-746, M102, 01205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfl1 1, (syn=SFiI1), (syn=φSFi11), (syn=ΦSi1 1), (syn=φSfi1 1), sfi19, (syn=SFi19), (syn=φSFi19), (syn=φSfi19), Sfi21, (syn=SFi21), (syn=φSFi21), (syn=φSfi21), ST0, STX, st2, ST2, ST4, S3, (syn=03), s265, 117, φ42, 157, φ80, φ81, φ82, φ83, φ84, φ85, φ86, φ87, φ88, φ89, φ90, φ91, φ92, φ93, φ94, φ95, φ96, φ97, φ98, φ99, φ100, φ101, φ102, φ227, Φ7201, ω1, ω2, ω3, ω4, ω5, ω6, ω8, ω1O, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/5T16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phages: CTXΦ, fs, (syn=si), fs2, Ivpf5, Vfl2, Vf33, VPIΦ, VSK, v6, 493, CP-T1, ET25, kappa, K139, Labol) XN-69P, OXN-86, O6N-21P, PB-I, P147, rp-1, SE3, VA-I, (syn=VcA-I), VcA-2, VP1, VP2, VP4, VP7, VP8, VP9, VP1O, VP17, VP18, VP19, X29, (syn=29 d'Herelle), t, THAWI-1, THAWI-2, THAWI-3, ΦHAWI-4, ΦHAWI-5, ΦHAWI-6, ΦHAWI-7, ΦHAWI-8, ΦHAWI-9, ΦHAWI-10, ΦHC1-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φ138, 1-II, 5, 13, 14, 16, 24, 32, 493, 6214, 7050, 7227, II, (syn=group II), (syn==φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, 06N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8, 1 1OA-1, 110A-5, 110A-7, by-1, OXN-52P, P13, P38, P53, P65, P108, Pill, TP13 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VP5, VPI1, VP15, VP16, α1, α2, α3a, α3b, 353B and HN-*Vibrio* (7).

Bacteria of the genus *Yersinia* are infected by the following phages: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In a specific embodiment, the bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus ViI, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus J598, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phil, *Escherichia* virus RB49, *Escherichia* virus HX01, *Escherichia* virus J509, *Escherichia* virus xRB 69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shf12, *Yersinia* virus D1, *Yersinia* virus PST, *Acinetobacter* virus 133, *Aeromonas* virus 65, *Aeromonas* virus Aeh1, *Escherichia* virus RB16, *Escheri*- chia virus RB32, *Escherichia* virus RB43, *Pseudomonas* virus 42, *Cronobacter* virus CR3, *Cronobacter* virus CR8, *Cronobacter* virus CR9, *Cronobacter* virus PBES02, *Pectobacterium* virus phiTE, *Cronobacter* virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus 13, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abpl, *Acinetobacter* virus Fril, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus ghl, *Prochlorococcus* virus PSSP7, *Synechococcus* virus P60, *Synechococcus* virus Syn5, *Streptococcus* virus Cp1, *Streptococcus* virus Cp1, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepi102, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, *Hamiltonella* virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wks13, *Escherichia* virus K1G, *Escherichia* virus K1H, *Escherichia* virus Klind1, *Escherichia* virus Klind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus 501, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littleo, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus 01205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escheri-* chia virus BF23, *Escherichia* virus DT57C, *Escherichia* virus EPS7, *Escherichia* virus FFH1, *Escherichia* virus H8, *Escherichia* virus s1ur09, *Escherichia* virus T5, *Salmonella* virus 118970sa12, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phi17, *Xanthomonas* virus Xop411, *Xanthomonas* virus Xp10, *Streptomyces* virus TP1604, *Streptomyces* virus YDN12, Alphaproteobacteria virus phiJ1001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, Spiroplasma virus SVTS2, *Stenotrophomonas* virus PSH1, *Stenotrophomonas* virus SMA6, *Stenotrophomonas* virus SMA7, *Stenotrophomonas* virus SMAS, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, Spiroplasma virus C74, Spiroplasma virus R8A2B, Spiroplasma virus SkV1CR23x, *Escherichia* virus FI, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, *Bdellovibrio* virus MAC1, *Bdellovibrio* virus MH2K, *Chlamydia* virus Chp1, *Chlamydia* virus Chp2, *Chlamydia* virus CPAR39, *Chlamydia* virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stxlphi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus ECO26_PO6, *Escherichia* virus ECO103_P15, *Escherichia* virus ECO103_P12, *Escherichia* virus ECO111 P16, *Escherichia* virus ECO111_P11, *Escherichia* virus VT2phi_272, *Escherichia* virus TL-2011c, *Escherichia* virus P13374, *Escherichia* virus Sp5.

In one embodiment, the bacteriophage derived particles target *E coli* and include the capsid of a bacteriophage selected in the group consisting of BW73, B278, D6, D108, E, E1, E24, E41, FI-2, FI-4, FI-5, HI8A, Ffl8B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, DD-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, al, 1, IA, 3, 3A, 3T+, 5φ, 9266Q, CFO103, HK620, J, K, K1F, m59, no. A, no. E, no. 3, no. 9, N4, sd, T3, T7, WPK, W31, ΔH, φC3888, φK3, φK7, φK12, φV-1, 104-CF, Φ05, Φ06, Φ07, φ1, φ1.2, φ20, φ95, φ263, φ1Ο92, φ1, φ11, Ω28, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J and 933H.

Origin of Replication

Origins of replication known in the art have been identified from species-specific plasmid DNAs (e.g. CoIE1, R1, pT181, pSC101, pMB1, R6K, RK2, p15a and the like), from bacterial virus (e.g. φX174, M13, F1 and P4) and from bacterial chromosomal origins of replication (e.g. oriC).

In one embodiment, the nucleic acid payload, for example a plasmid, comprises a bacterial origin of replication that is functional in the targeted bacteria.

Alternatively, the nucleic acid payload, for example a plasmid, does not comprise a functional bacterial origin of replication or contains an origin of replication that is inactive in the targeted bacteria. Thus, the nucleic acid payload cannot replicate by itself once it has been introduced into a bacterium by the bacterial virus particle.

In one embodiment, the origin of replication on the nucleic acid payload, for example a plasmid, to be packaged is inactive in the targeted bacteria, meaning that this origin of replication is not functional in the bacteria targeted by the bacterial virus particles, thus preventing unwanted payload replication.

In one embodiment, the nucleic acid payload, for example a plasmid, comprises a bacterial origin of replication that is functional in the bacteria used for the production of the bacterial virus particles.

Bacteria-Specific Origins of Replication

Plasmid replication depends on host enzymes and on plasmid-controlled cis and trans determinants. For example, some plasmids have determinants that are recognized in almost all gram-negative bacteria and act correctly in each host during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microhio and Molec Biol. Rev 62:434-464) that start at the origin of replication. This replication origin contains sites that are required for interactions of plasmid and/or host encoded proteins.

Origins of replication used on the nucleic acid payload, for example a plasmid, may be moderate copy number, such as ColE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In an embodiment, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10.

In an embodiment, the bacterial origin of replication is selected in the group consisting of pC194, pE194, BBR1, pBC1, pEP2, pWVO1, pLF1311, pAP1, pWKS1, pLS1, pLS11, pUB6060, pJD4, 0E01, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In a particular embodiment, the bacterial origin of replication are ColE1 and p15a.

In one embodiment, the bacterial origin of replication is functional in *Propionibacterium* and *Cutibacterium* more specifically in *Propionibacterium freudenreichii* and *Cutibacterium acnes* and is selected from the group consisting of pLME108, pLME106, p545, pRGO1, pZGX01, pPG01, pYS1, FRJS12-3, FRJS25-1, pIMPLE-HL096PA1, A_15_1_R1.

Phage Origins of Replication

The payload may comprise a phage replication origin which can initiate, with complementation of a complete phage genome, the replication of the payload for later encapsulation into the different capsids.

A phage origin can also be engineered to act as a bacterial origin of replication without the need to package any phage particles.

A phage origin of replication comprised in the payload can be any origin of replication found in a phage.

In an embodiment, the phage origin of replication can be the wild-type or non-wildtype sequence of the M13, f1, φX174, P4, Lambda, P2, 186, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

In an embodiment, the phage origin of replication is selected in the group consisting of phage origins of replication of M13, f1, φX174, P4, and Lambda.

In a particular embodiment, the phage origin of replication is the P4 origin of replication.

In a particular embodiment, the phage origin of replication is from *Propionibacterium* phages: BW-like phages such as Doucette,B22,E6,G4, BV-like phages such as Anatole,E1,B3, BX-like phages such as PFR1 and PFR2, filamentous B5 phage, BU-like phages (*Cutibacterium acnes* phages).

The bacteria targeted by the bacteriophage derived particles can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the type of bacteriophages being used for preparing the bacterial virus particles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus: *Yersinia* spp., *Escherichia* spp., *Klebsiella* spp., *Acinetobacter* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucella* spp., *Campylobacter* spp., *Chlamydophilia* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Lactobacillus* spp., *Faecalibacterium* spp., *Ruminococcus* spp. and a mixture thereof.

Thus, bacteriophage derived particles may target (e.g., specifically target) a bacterial cell from any one or more of the foregoing genera of bacteria to specifically deliver the payload as described herein.

In an embodiment, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, bacterial cells are anaerobic bacterial cells (e.g., cells that do not require oxygen for growth). Anaerobic bacterial cells include facultative anaerobic cells such as but not limited to *Escherichia coli*, *Shewanella oneidensi*, *Gardnerella vaginalis* and *Listeria*. Anaerobic bacterial cells also include obligate anaerobic cells such as, for example, *Bacteroides*, *Clostridium*, *Cutibacterium*, *Propionibacterium*, *Fusobacterium* and *Porphyromonas* species. In humans, anaerobic bacteria are most commonly found in the gastrointestinal tract. In some particular embodiments, the targeted bacteria are thus bacteria most commonly found in the gastrointestinal tract. Bacteriophages used for preparing the bacterial virus particles, and then the bacterial virus particles, may target (e.g., to specifically target) anaerobic bacterial cells according to their specific spectra known by the person skilled in the art to specifically deliver the plasmid.

In some embodiments, the targeted bacterial cells are selected from the group consisting of *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain *PCC6803, Bacillus liquefaciens, Pyrococcus abyssi, Selenomonas nominantium, Lactobacillus hilgardii, Streptococcus fetus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fusobacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes* (formerly *Propionibacterium acnes*), *Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas* aerigunosa, and a mixture thereof preferably the bacteria of interest are selected from the group consisting of *Escherichia coli, Enterococcus faecium, Staphylococcus aureus, Klebsiella pneumoniae, Acinetobacter baumanii, Pseudomonas aeruginosa, Enterobacter cloacae,* and *Enterobacter aerogenes*, and a mixture thereof.

In some embodiments, the targeted bacterial cells are selected from the group consisting of *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter, Weisella, Clostridium, Bacteroides, Ruminococcus, Faecalibacterium, Treponema, Phascolarctobacterium, Megasphaera, Faecalibacterium, Bifidobacterium, Lactobacillus, Sutterella,* and *Prevotella*.

In other embodiments, the targeted bacteria cells are selected from the group consisting of *Achromobacter xylosoxidans, Acidaminococcus fermentans, Acidaminococcus intestini, Acidaminococcus* sp., *Acinetobacter baumannii, Acinetobacter junii, Acinetobacter lwoffii, Actinobacillus capsulatus, Actinomyces naeslundii, Actinomyces neuii, Actinomyces odontolyticus, Actinomyces radingae, Adlercreutzia equolifaciens, Aeromicrobium massiliense, Aggregatibacter actinomycetemcomitans, Akkermansia muciniphila, Aliagarivorans marinus, Alistipes fine goldii, Alistipes indistinctus, Alistipes inops, Alistipes onderdonkii, Alistipes putredinis, Alistipes senegalensis, Alistipes shahii, Alistipes timonensis, Alloscardovia omnicolens, Anaerobacter polyendosporus, Anaerobaculum hydrogeniformans, Anaerococcus hydrogenalis, Anaerococcus prevotii, Anaerococcus senegalensis, Anaerofustis stercorihominis, Anaerostipes caccae, Anaerostipes hadrus, Anaerotruncus colihominis, Aneurinibacillus aneurinilyticus, Bacillus licheniformis, Bacillus massilioanorexius, Bacillus massiliosenegalensis, Bacillus simplex, Bacillus smithii, Bacillus subtilis, Bacillus thuringiensis, Bacillus timonensis, Bacteroides xylanisolvens, Bacteroides acidifaciens, Bacteroides caccae, Bacteroides capillosus, Bacteroides cellulosilyticus, Bacteroides clarus, Bacteroides coprocola, Bacteroides coprophilus, Bacteroides dorei, Bacteroides eggerthii, Bacteroides faecis, Bacteroides finegoldii, Bacteroides fluxus, Bacteroides fragilis, Bacteroides gallinarum, Bacteroides intestinalis, Bacteroides nordii, Bacteroides oleiciplenus, Bacteroides ovatus, Bacteroides pectinophilus, Bacteroides plebeius, Bacteroides salanitronis, Bacteroides salyersiae, Bacteroides* sp., *Bacteroides stercoris, Bacteroides thetaiotaomicron, Bacteroides uniformis, Bacteroides vulgatus, Bacteroides xylanisolvens, Bacteroidespectinophilus ATCC, Barnesiella intestinihominis, Bavariicoccus seileri, Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium longum, Bifidobacterium pseudocatenulatum, Bifidobacterium stercoris, Bilophila wadsworthia, Blautia faecis, Blautia hansenii, Blautia hydrogenotrophica, Blautia luti, Blautia obeum, Blautia producta, Blautia wexlerae, Brachymonas chironomi, Brevibacterium senegalense, Bryantella formatexigens, butyrate*-producing *bacterium, Butyricicoccus pullicaecorum, Butyricimonas virosa, Butyrivibrio crossotus, Butyrivibrio fibrisolvens, Caldicoprobacter faecalis, Campylobacter concisus, Campylobacter jejuni, Campylobacter upsaliensis, Catenibacterium mitsuokai, Cedecea*

*davisae, Cellulomonas massiliensis, Cetobacterium somerae, Citrobacter braakii, Citrobacter freundii, Citrobacter pasteurii, Citrobacter* sp., *Citrobacter youngae, Cloacibacillus evryensis, Clostridiales bacterium, Clostridioides difficile, Clostridium asparagiforme, Clostridium bartlettii, Clostridium boliviensis, Clostridium bolteae, Clostridium hathewayi, Clostridium hiranonis, Clostridium hylemonae, Clostridium leptum, Clostridium methylpentosum, Clostridium nexile, Clostridium orbiscindens, Clostridium ramosum, Clostridium scindens, Clostridium* sp, *Clostridium* sp., *Clostridium spiroforme, Clostridium sporogenes, Clostridium symbiosum, Collinsella aerofaciens, Collinsella intestinalis, Collinsella stercoris, Collinsella tanakaei, Coprobacillus cateniformis, Coprobacter fastidiosus, Coprococcus catus, Coprococcus comes, Coprococcus eutactus, Corynebacterium ammoniagenes, Corynebacterium amycolatum, Corynebacterium pseudodiphtheriticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancero* genus, *Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus* sp., *Enterovibrio nigricans, Erysipelatoclostridium ramosum, Escherichia coli, Escherichia* sp., *Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium* cf, *Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium* sp., *Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemanella biformis, Holdemania fdiformis, Holdemania filiformis, Holdemania massiliensis, Holdemaniafiliformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillusplantarum* subsp., *Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithiiFl, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oxalis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteuspenneri* ATCC, *Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus* sp, *Ruminococcus* sp., *Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oxalis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis, unknown sp, unknown* sp., *Varibaculum cambriense, Veillonella atypica, Veillonella dispar, Veillonella parvula, Vibrio cincinnatiensis, Virgibacillus salexigens, Weissella paramesenteroides,* and *Weissellaparamesenteroides* ATCC.

In other embodiments, the targeted bacteria cells are those commonly found on the skin microbiota and are preferably selected from the group consisting of *Acetobacter farinalis, Acetobacter malorum, Acetobacter orleanensis, Acetobacter sicerae, Achromobacter anxifer, Achromobacter denitrifi-* cans, Achromobacter marplatensis, Achromobacter spanius, Achromobacter xylosoxidans subsp. xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosospora, Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila subsp. hydrophila, Aeromonas piscicola, Aeromonas popoffii, Aeromonas rivuli, Aeromonas salmonicida subsp. pectinolytica, Aeromonas salmonicida subsp. smithia, Amaricoccus kaplicensis, Amaricoccus veronensis, Aminobacter aganoensis, Aminobacter ciceronei, Aminobacter lissarensis, Aminobacter niigataensis, Ancylobacter polymorphus, Anoxybacillus flavithermus subsp. yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans subsp. lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense subsp. putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii subsp. bulgaricus, Lactobacillus modestisalitolerans, Lactobacillus plantarum subsp. argentoratensis, Lactobacillus xiangfangensis, Lechevalieria roselyniae, Lentzea albida, Lentzea californiensis, Leuconostoc carnosum, Leuconostoc citreum, Leuconostoc gelidum subsp. gasicomitatum, Leuconostoc mesenteroides subsp. suionicum, Luteimonas aestuarii, Lysobacter antibioticus, Lysobacter koreensis, Lysobacter oryzae, Magnetospirillum moscoviense, Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydans, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogenes, Micromonospora rhizosphaerae, Micromonospora saelicesensis, Microvirga subterranea, Microvirga zambiensis, Mycobacterium alvei, Mycobacterium avium subsp. silvaticum, Mycobacterium colombiense, Mycobacterium conceptionense, Mycobacterium conceptionense, Mycobacterium farcinogenes, Mycobacterium fortuitum subsp. fortuitum, Mycobacterium goodii, Mycobacterium insubricum, Mycobacterium llatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia lijiangensis, Nocardia thailandica, Novosphingobium barchaimii, Novosphingobium lindaniclasticum, Novosphingobium lindaniclasticum, Novosphingobium mathurense, Ochrobactrum pseudogrignonense, Oxalicibacterium solurbis, Paraburkholderia glathei, Paraburkholderia humi, Paraburkholderia phenazinium, Paraburkholderia phytofirmans, Paraburkholderia sordidicola, Paraburkholderia terricola, Paraburkholderia xenovorans, Paracoccus laeviglucosivorans, Patulibacter ginsengiterrae, Polymorphospora rubra, Porphyrobacter colymbi, Prevotella jejuni, Prevotella melaninogenica, Propionibacterium acnes subsp. elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacter ginsenosidimutans, Rheinheimera japonica, Rheinheimera muenzenbergensis, Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica subsp. salamae, Serratia ficaria, Serratia myotis, Serratia vespertilionis, Shewanella aestuarii, Shewanella decolorationis, Sphingobium amiense, Sphingobium baderi, Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis, Sphingopyxis fribergensis, Sphingopyxis granuli, Sphingopyxis indica, Sphingopyxis witflariensis, Staphylococcus agnetis, Staphylococcus aureus subsp. aureus, Staphylococcus epidermidis, Staphylococcus hominis subsp. novobiosepticus, Staphylococcus nepalensis, Staphylococcus saprophyticus subsp. bovis, Staphylococcus sciuri subsp. carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii subsp. anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibacter segnis, Agrococcus baldri, Albibacter methylovorans, Alcaligenes faecalis subsp. faecalis, Algoriphagus ratkowskyi, Alkalibacterium olivapovliticus, Alkalibacterium pelagium, Alkalibacterium pelagium, Alloprevotella cava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans subsp. lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus subsp. caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum subsp. polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas sulfidaeris, Herpetosiphon aurantiacus, Hydrocarboniphaga effusa, Idiomarina maxis, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oxalis, Klebsiella oxytoca, Knoellia aerolata, Knoellia locipacati, Kocuria atrinae, Kocuria camiphila, Kocuria kristinae, Kocuria palustris, Kocuria turfanensis, Lachnoanaerobaculum saburreum, Lachnoanaerobaculum saburreum, Lactobacillus crispatus, Lactobacillus iners, Lactococcus lactis subsp. lactis, Lactococcus lactis subsp. lactis, Lactococcus piscium, Lapillicoccus jejuensis, Lautropia mirabilis, Legionella beliardensis, Leptotrichia buccalis, Leptotrichia goodfellowii, Leptotrichia hofstadii, Leptotrichia hongkongensis, Leptotrichia shahii, Leptotrichia trevisanii, Leptotrichia wadei, Luteimonas terricola, Lysinibacillus fusiformis, Lysobacter spongiicola, Lysobacter xinjiangensis, Macrococcus caseolyticus, Marmoricola pocheonensis, Marmoricola scoriae, Massilia alkalitolerans, Massilia alkalitolerans, Massilia aurea, Massilia plicata, Massilia timonae, Megamonas rupellensis, Meiothermus silvanus, Methylobacterium dankookense, Methylobacterium goesingense, Methylobacterium goesingense, Methylobacterium isbiliense, Methylobacterium jeotgali, Methylobacterium oxalidis, Methylobacterium platani, Methylobacterium pseudosasicola, Methyloversatilis universalis, Microbacterium foliorum, Microbacterium hydrothermale, Microbacterium hydrothermale, Microbacterium lacticum, Microbacterium lacticum, Microbacterium laevamformans, Microbacterium paludicola, Microbacterium petrolearium, Microbacterium phyllosphaerae, Microbacterium resistens, Micrococcus antarcticus, Micrococcus cohnii, Micrococcus flavus, Micrococcus lylae, Micrococcus terreus, Microlunatus aurantiacus, Micropruina glycogenica, Microvirga aerilata, Microvirga aerilata, Microvirga subterranea, Microvirga vignae, Microvirga zambiensis, Microvirgula aerodenitrificans, Mogibacterium timidum, Moraxella atlantae, Moraxella catarrhalis, Morganella morganii subsp. morganii, Morganella psychrotolerans, Murdochiella asaccharolytica, Mycobacterium asiaticum, Mycobacterium chubuense, Mycobacterium crocinum, Mycobacterium gadium, Mycobacterium holsaticum, Mycobacterium iranicum, Mycobacterium longobardum, Mycobacterium neoaurum, Mycobacterium neoaurum, Mycobacterium obuense, Negativicoccus succinicivorans, Neisseria bacilliformis, Neisseria oralis, Neisseria sicca, Neisseria subflava, Nesterenkonia lacusekhoensis, Nesterenkonia rhizosphaerae, Nevskia persephonica, Nevskia ramosa, Niabella yanshanensis, Niveibacterium umoris, Nocardia niwae, Nocardia thailandica, Nocardioides agariphilus, Nocardioides dilutus, Nocardioides ganghwensis, Nocardioides hwasunensis, Nocardioides nanhaiensis, Nocardioides sediminis, Nosocomiicoccus ampullae, Noviherbaspirillum malthae, Novosphingobium lindaniclasticum, Novosphingobium rosa, Ochrobactrum rhizosphaerae, Olsenella uli, Ornithinimicrobium murale, Ornithinimicrobium tianjinense, Oryzobacter terrae, Ottowia beijingensis, Paenalcaligenes suwonensis, Paenibacillus agaridevorans, Paenibacillus phoenicis, Paenibacillus xylanexedens, Paludibacterium yongneupense, Pantoea cypripedii, Parabacteroides distasonis, Paraburkholderia andropogonis, Paracoccus alcaliphilus, Paracoccus angustae, Paracoccus kocurii, Paracoccus laeviglucosivorans, Paracoccus sediminis, Paracoccus sphaerophysae, Paracoccus yeei, Parvimonas micra, Parviterribacter multiflagellatus, Patulibacter ginsengiterrae, Pedobacter aquatilis, Pedobacter ginsengisoli, Pedobacter xixiisoli, Peptococcus niger, Peptoniphilus coxii, Peptoniphilus gorbachii, Peptoniphilus harei, Peptoniphilus koenoeneniae, Peptoniphilus lacrimalis, Peptostreptococcus anaerobius, Peptostreptococcus stomatis, Phascolarctobacterium faecium, Phenylobacterium haematophilum, Phenylobacterium kunshanense, Pluralibacter gergoviae, Polymorphobacter multimamfer, Porphyromonas bennonis, Porphyromonas endodontalis, Porphyromonas gingivalis, Porphyromonas gingivicanis, Porphyromonas pasteri, Porphyromonas pogonae, Porphyromonas somerae, Povalibacter uvarum, Prevotella aurantiaca, Prevotella baroniae, Prevotella bivia, Prevotella buccae, Prevotella buccalis, Prevotella copri, Prevotella corporis, Prevotella denticola, Prevotella enoeca, Prevotella histicola, Prevotella intermedia, Prevotella jejuni, Prevotella jejuni, Prevotella maculosa, Prevotella melaninogenica, Prevotella melaninogenica, Prevotella micans, Prevotella multiformis, Prevotella nanceiensis, Prevotella nigrescens, Prevotella oris, Prevotella oulorum, Prevotella pallens, Prevotella pleuritidis, Prevotella saccharolytica, Prevotella salivae, Prevotella shahii, Prevotella timonensis, Prevotella veroralis, Propionibacterium acidifaciens, Propionibacterium acnes subsp. acnes, Propionibacterium acnes subsp. acnes, Propionibacterium acnes subsp. elongatum, Propionibacterium granulosum, Propionimicrobium lymphophilum, Propionispira arcuata, Pseudokineococcus lusitanus, Pseudomonas aeruginosa, Pseudomonas chengduensis, Pseudonocardia benzenivorans, Pseudorhodoplanes sinuspersici, Psychrobacter sanguinis, Ramlibacter ginsenosidimutans, Rheinheimera aquimaris, Rhizobium alvei, Rhizobium daejeonense, Rhizobium larrymoorei, Rhizobium rhizoryzae, Rhizobium soli, Rhizobium taibaishanense, Rhizobium vignae, Rhodanobacter glycinis, Rhodobacter veldkampii, Rhodococcus enclensis, Rhodococcus fascians, Rhodococcus fascians, Rhodovarius lipocyclicus, Rivicola pingtungensis, Roseburia inulinivorans, Rosenbergiella nectarea, Roseomonas aerilata, Roseomonas aquatica, Roseomonas mucosa, Roseomonas rosea, Roseomonas vinacea, Rothia aeria, Rothia amarae, Rothia dentocariosa, Rothia endophytica, Rothia mucilaginosa, Rothia nasimurium, Rubellimicrobium mesophilum, Rubellimicrobium roseum, Rubrobacter bracarensis, Rudaea cellulosilytica, Ruminococcus gnavus, Runella zeae, Saccharopolyspora rectivirgula, Salinicoccus qingdaonensis, Scardovia wiggsiae, Sediminibacterium ginsengisoli, Selenomonas artemidis, Selenomonas infelix, Selenomonas noxia, Selenomonas sputigena, Shewanella aestuarii, Shuttleworthia satelles, Simonsiella muelleri, Skermanella aerolata, Skermanella stibiiresistens, Slackia exigua, Smaragdicoccus niigatensis, Sneathia sanguinegens, Solirubrobacter soli, Sphingobacterium caeni, Sphingobacterium daejeonense, Sphingobacterium hotanense, Sphingobacterium kyonggiense, Sphingobacterium multivorum, Sphingobacterium nematocida, Sphingobacterium spiritivorum, Sphingobium amiense, Sphingobium indicum, Sphingobium lactosutens, Sphingobium subterraneum, Sphingomonas abaci, Sphingomonas aestuarii, Sphingomonas canadensis, Sphingomonas daechungensis, Sphingomonas dokdonensis, Sphingomonas echinoides, Sphingomonas fonticola, Sphingomonas fonticola, Sphingomonas formosensis, Sphingomonas gei, Sphingomonas hankookensis, Sphingomonas hankookensis,

*Sphingomonas koreensis, Sphingomonas kyeonggiensis, Sphingomonas laterariae, Sphingomonas mucosissima, Sphingomonas oligophenolica, Sphingomonas pseudosanguinis, Sphingomonas sediminicola, Sphingomonas yantingensis, Sphingomonas yunnanensis, Sphingopyxis indica, Spirosoma rigui, Sporacetigenium mesophilum, Sporocytophaga myxococcoides, Staphylococcus auricularis, Staphylococcus epidermidis, Staphylococcus epidermidis, Staphylococcus hominis subsp. novobiosepticus, Staphylococcus lugdunensis, Staphylococcus pettenkoferi, Stenotrophomonas koreensis, Stenotrophomonas rhizophila, Stenotrophomonas rhizophila, Streptococcus agalactiae, Streptococcus canis, Streptococcus cristatus, Streptococcus gordonii, Streptococcus infantis, Streptococcus intermedius, Streptococcus mutans, Streptococcus oligofermentans, Streptococcus oxalis, Streptococcus sanguinis, Streptomyces iconiensis, Streptomyces yanglinensis, Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida* and *Zoogloea caeni.*

In other embodiments, the targeted bacteria cells are those commonly found in the vaginal microbiota and are preferably selected from the group consisting of *Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyongiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum* subsp. *infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens Corynebacterium nuruki, Corynebacterium pseudo genitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus* ultunensis, Lactobacillus vaginalis, Lactococcus lactis, Leptotrichia buccalis, Leuconostoc camosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odoribacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oxalis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae and Zoogloea ramigera.

In one embodiment, the targeted bacteria are *Escherichia coli*.

In one embodiment, the targeted bacteria are *Cutibacterium acnes*, more specifically the acne related *Cutibacterium acnes* from the phylogroup IA1 or RT4, RT5, RT8, RT9, RT10 or Clonal Complex (CC) CC1, CC3, CC4, more specifically the ST1, ST3, ST4.

Thus, bacteriophages used for preparing the bacterial virus particles, and then the bacterial virus particles, may target (e.g., specifically target) a bacterial cell from any one or more of the foregoing genera and/or species of bacteria to specifically deliver the payload.

In one embodiment, the targeted bacteria are pathogenic bacteria. The targeted bacteria can be virulent bacteria.

The targeted bacteria can be antibacterial resistance bacteria, for example, selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. In a specific embodiment, the targeted bacteria can be selected from the group consisting of extended-spectrum beta-lactamase-producing (ESBL) *Escherichia coli* strains.

Alternatively, the targeted bacterium can be a bacterium of the microbiome of a given species, for example a bacterium of the human microbiota.

In one aspect, synthetic bacterial delivery vehicles with desired target host ranges are provided for use in transfer of a nucleic acid payload of interest to a target bacterial cell. The synthetic bacterial delivery vehicles may be characterized by a chimeric receptor binding protein (RBP), wherein the chimeric RBP comprises a fusion between the N-terminal domain of a RBP from a lambda-like bacteriophage, or lambda bacteriophage, and the C-terminal domain of a different RBP. It has been demonstrated that a significant portion of a lambda-like RBP, such as a stf protein, can be exchanged with a portion of a different RBP.

As used herein, a receptor binding protein or RBP is a polypeptide that recognizes, and optionally binds and/or modifies or degrades a substrate located on the bacterial outer envelope, such as, without limitation, bacterial outer membrane, LPS, capsule, protein receptor, channel, structure such as the flagellum, pili, secretion system. The substrate can be, without limitation, any carbohydrate or modified carbohydrate, any lipid or modified lipid, any protein or modified protein, any amino acid sequence, and any combination thereof.

The present disclosure also provides synthetic bacterial delivery vehicles that are characterized by the presence of an engineered branched receptor binding multi-subunit protein complex ("branched-RBP"). Such delivery vehicles may be used to transfer a nucleic acid payload of interest into a target bacterial cell. The engineered branched-RBP comprises two or more associated receptor binding proteins, derived from bacteriophages, which associate with one another based on the presence of interaction domains (IDs). The association of one subunit with another can be non-covalent or covalent. Each of the polypeptide subunits contain IDs that function as "anchors" for association of one subunit RBP with another. In specific embodiments, the branched-RBP may comprise multiple RBP subunits, including, for example, two, three, four, etc. subunits.

For disclosure of recombinant bacterial delivery vehicles, see U.S. Provisional Application Ser. Nos. 62/849,108, 62/849,112, 62/802,777, 62/771,761 and 62/783,258, each of which is incorporated herein in their entirety.

As used herein, the term "nucleic acid payload" refers to any nucleic acid sequence or amino acid sequence, or a combination of both (such as, without limitation, peptide nucleic acid or peptide-oligonucleotide conjugate) transferred into a bacterium with a delivery vehicle. In an embodiment, the term "nucleic acid payload" refers to any nucleic acid sequence, optionally in combination with an amino acid sequence (such as, without limitation, peptide nucleic acid or peptide-oligonucleotide conjugate) transferred into a bacterium with a delivery vehicle. The nucleic acid payload is designed to encode a protein or nucleic acid of interest, for transfer into a desired target bacterial host cell. The term "nucleic acid payload" may refer to a plasmid, a vector or a cargo. The nucleic acid payload can be a phagemid or phasmid obtained from natural, evolved or engineered bacteriophage genome. The nucleic acid payload can also be composed only in part of phagemid or phasmid obtained from natural, evolved or engineered bacteriophage genome. The nucleic acid payload is, for example, a nucleic acid sequence packaged in a bacterial delivery vehicle, for example in a bacteriophage-derived capsid.

Described herein are engineered bacterial delivery vehicles, with desired target bacterial cell specificity and/or host range, comprising a nucleic acid payload having an embedded unique tracer nucleotide sequence tag. As used herein "multivalent mixture of delivery vehicles "refers to a mixture of one or more different, or dissimilar, bacterial delivery vehicles. Such bacterial delivery vehicles may differ because they possess at least one structural feature that distinguishes them from other bacterial delivery vehicles within the mixture. Such structural features include, for example, differences in bacterial cell binding capabilities and/or host range that may arise for example through differences in expressed RBPs within the delivery vehicle. A multivalent mixture thus comprises at least two distinct populations of bacterial delivery vehicles.

The present disclosure provides pharmaceutical or veterinary composition comprising a multivalent mixture of bacterial delivery vehicles as defined herein, i.e. comprising at least two different bacterial delivery vehicles, wherein each bacterial delivery vehicle comprises a nucleic acid payload with a unique tracer nucleic acid sequence. The pharmaceutical or veterinary composition may be prepared as a sterile solid composition that may be suspended at the time of administration using sterile water, saline, or other appropriate sterile injectable medium. The pharmaceutical or veterinary compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The particles can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacteriophage derived particles disclosed herein may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

The present disclosure relates to use of the disclosed pharmaceutical or veterinary composition in the treatment of a disease or disorder caused by bacteria. It also relates to a method for treating a disease or disorder caused by bacteria comprising administering to a subject having said disease or disorder in need of treatment a pharmaceutical or veterinary composition disclosed herein. It further relates to the use of a pharmaceutical or veterinary composition provided herein for the manufacture of a medicament for the treatment of a disease or disorder caused by bacteria.

In one embodiment, the disease or disorder caused by bacteria may be selected from the group consisting of skin chronic inflammation such as acne (acne vulgaris), progressive macular hypomelanosis, abdominal cramps, acute epiglottitis, arthritis, bacteraemia, bloody diarrhea, botulism, Brucellosis, brain abscess, cardiomyopathy, chancroid venereal disease, *Chlamydia*, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myocarditis, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection, whooping cough, Nonalcoholic Fatty Liver Disease (NASH).

In another embodiment, the disease or disorder caused by bacteria is an infection caused by bacteria, for example, those selected from the group consisting of intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, and a combination thereof. In an embodiment, the infection is caused by a bacterium presenting an antibiotic resistance. In a particular embodiment, the infection is caused by a bacterium as listed above in the targeted bacteria.

In another embodiment, the disease or disorder caused by bacteria is a metabolic disorder such as obesity and diabetes.

In a particular embodiment, the disclosure provides a pharmaceutical or veterinary composition for use in the treatment of a pathology involving bacteria of the human microbiome, such as inflammatory and auto-immune diseases, cancers, infections or brain disorders. It also provides a method for treating a pathology involving bacteria of the human microbiome comprising administering to a subject having said pathology in need of treatment a pharmaceutical or veterinary composition provided herein. It further concerns the use of such pharmaceutical or veterinary composition for the manufacture of a medicament for the treatment of a pathology involving bacteria of the human microbiome. Indeed, some bacteria of the microbiome, without triggering any infection, can secrete molecules that will induce and/or enhance inflammatory or auto-immune diseases or cancer development. More specifically, the present disclosure relates also to modulating microbiome compositions to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the present disclosure is a method for controlling the microbiome of a subject, comprising administering an effective amount of the pharmaceutical composition as disclosed herein in said subject.

In a particular embodiment, a method is provided for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition provided herein capable of recognizing each pathogenic bacterial strain or species identified in the sample and to deliver the packaged payload. The disclosure further relates to and provides a) a pharmaceutical or veterinary composition for use in the treatment of a bacterial infection in an individual, or b) the use of a pharmaceutical or veterinary composition for the manufacture of a medicament in the treatment of a bacterial infection in an individual, wherein, in a) or b), the preparation of the pharmaceutical or veterinary composition comprises: (i) providing a biological sample from the individual and determining a group of bacterial DNA sequences from the sample; ii) based on the determining of the sequences, identifying one or more pathogenic bacterial strains or species that were in the sample; and iii) preparing a pharmaceutical or veterinary composition capable of recognizing each pathogenic bacterial strain or species identified in the sample and to deliver the packaged payload.

In an embodiment, the biological sample comprises pathological and non-pathological bacterial species, and subsequent to administering the pharmaceutical or veterinary composition disclosed herein to the individual, the amount of pathogenic bacteria on or in the individual is reduced, but the amount of non-pathogenic bacteria is not reduced.

In another particular embodiment, a pharmaceutical or veterinary composition is provided for use in order to improve the effectiveness of drugs. Indeed, some bacteria of the microbiome, without being pathogenic by themselves, are known to be able to metabolize drugs and to modify them in ineffective or harmful molecules.

In another particular embodiment, the present disclosure relates to the in-situ bacterial production of any compound of interest, including therapeutic compound such as prophylactic and therapeutic vaccine for mammals. The compound of interest can be produced inside the targeted bacteria, secreted from the targeted bacteria or expressed on the surface of the targeted bacteria. In a more particular embodiment, an antigen is expressed on the surface of the targeted bacteria for prophylactic and/or therapeutic vaccination.

The present disclosure also relates to a non-therapeutic use of the bacterial delivery particles. For instance, the non-therapeutic use can be a cosmetic use or a use for improving the well-being of a subject, in particular a subject who does not suffer from a disease. Accordingly, the present disclosure also relates to a cosmetic composition or a non-therapeutic composition comprising the bacteriophage derived particles provided herein.

Subject, Regimen and Administration

The subject to be treated by the compositions provided herein includes an animal, for example a mammal. In a particular embodiment the animal is a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject may be a human at the prenatal stage, a new-born, a child, an infant, an adolescent or an adult at any age.

In an embodiment, the subject has been diagnosed with, or is at risk of developing an infection, a disorder and/or a disease due to a bacterium. Diagnostic method of such infection, disorder and/or disease are well known by one skilled in the art.

In a particular embodiment, the infection, disorder and/or disease is caused by a bacterium presenting a resistance to treatment, for example, the infection, disorder or disease is caused by a bacterium presenting an antibiotic resistance.

In a particular embodiment, the subject has never received any treatment prior to the administration of the provided delivery vehicles, for example, a payload, particularly a payload packaged into a delivery vehicle, for example, a packaged plasmid or phagemid into a bacterial virus particle, or of a pharmaceutical or veterinary composition as provided herein.

In a particular embodiment, the subject has already received at least one line of treatment. In non-limiting embodiments, the subject has already received two or more lines of treatment, prior to the administration of the provided delivery vehicles, for example, a payload, particularly a payload packaged into a delivery vehicle, for example a packaged plasmid or phagemid into a bacterial virus particle, or of a pharmaceutical or veterinary composition as disclosed herein.

In an embodiment, the treatment is administered regularly. In non-limiting embodiments, the treatment is administered preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

In an embodiment the duration of treatment with delivery vehicles provided herein, for example a payload, particularly a payload packaged into a delivery vehicle, for example, a packaged plasmid or phagemid into a bacterial virus particle, or with a pharmaceutical or veterinary composition, preferably comprises between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of delivery vehicles provided herein, for example of a payload, particularly of a payload packaged into a delivery vehicle, for example a packaged plasmid or phagemid into a bacterial virus particle, or of a pharmaceutical or veterinary composition can be adjusted by one skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of delivery vehicles, for example a payload, particularly a payload packaged into a delivery vehicle, for example a packaged plasmid or phagemid into a bacterial virus particle, or of a pharmaceutical or veterinary composition, to be administered will be determined by standard procedure well known by those of ordinary skills in the art. Physiological data of the patient or subject (e.g. age, size, and weight) and the routes of administration will be taken into account to determine the appropriate dosage, so as a therapeutically effective amount will be administered to the patient or subject.

For example, the total amount of delivery vehicles, particularly a payload packaged into a delivery vehicle, for example, a plasmid or phagemid packaged into a bacterial virus particle, for each administration comprises between $10^4$ and $10^{15}$ delivery vehicles.

As used herein, "tracer" refers to a nucleic acid sequence associated with, i.e., embedded, within a nucleic acid payload. The tracer acts as a bacterial delivery vehicle "identification tag" that may be used to assess the presence and/or amount of a bacterial delivery vehicle within a multivalent mixture of bacterial delivery vehicles. As disclosed herein, the tracer may be embedded within a non-coding region, a coding region and/or 5' or 3' untranslated regions of a nucleic acid payload.

The tracer may be any nucleic acid sequence the detection of which is correlated with the presence of a specific bacterial delivery vehicle. Thus, in the mixture, each population of bacterial delivery vehicles comprises a distinct and unique tracer. Detection of the tracer sequences may be achieved using a variety of different detection methods well known to those of skill in the art. In a specific embodiment, the tracer sequences may act as binding sites for one or multiple primer(s) design to be used in conjunction with amplification procedures, such as PCR reactions. The tracers may be designed to include constant regions to which primers may bind for amplification of tracers within a mixture of bacterial delivery vehicles. In an embodiment, constant regions may be identical in all tracers of the multivalent mixture. Such constant region binding primers may be used to amplify in total all of the tracers within a mixture of bacterial delivery vehicles. The tracers may be designed to include variable regions to which primers may bind for amplification of tracers within a mixture of bacterial delivery vehicles. The variable region binding primers may be used to identify specific bacterial delivery vehicles within a mixture. In one aspect, the variable regions are positioned within a barcode.

One or more rounds of amplifications may be performed for identification and/or quantification of the bacterial delivery vehicles within a mixture. In specific embodiments, mixtures of different types of primers may be used in each of the amplification reactions. For example, primers that bind only to the constant regions, primers that bind only to the variable regions and/or primers that overlap the constant and the variable regions may be used. Alternatively, for amplification reactions, a primer that binds to a constant region and a primer that binds to a variable region may be used. Depending on the primers used, the amplification reaction may result in amplification in total of the mixture of tracers found within a mixture of bacterial delivery vehicles. Alternatively, the primers may be selected to amplify specific bacterial delivery vehicles within a mixture.

In a specific embodiment, primers that bind to the tracer constant regions may be used for a first round of amplification following by a subsequent second round of amplification reactions using, for example, primers that bind to a variable region within the tracer, to further assess the presence of specific delivery vehicles within a mixture of vehicles.

As described in detail below, one or more features are to be considered in the design and of tracer sequences for use in bacterial delivery vehicle identification. Such features include, for example, primer binding site length, melting temperature and percent G/C content each of which may affect the effectiveness of, for example, an amplification reaction. Still further, the tracer should be designed so as to minimally interfere with the growth properties of the bacterial delivery vehicle packaging cell line or target bacterial cell. The tracer should minimally affect the production of the delivery vehicles within the packaging cell line. Inclusion of undesired restriction enzyme cleavage sites should be avoided. Finally, regions of homology with packaging cell DNA, target host DNA or payload DNA should be avoided in tracers as such regions of homology may act as sites for undesired homologous recombination.

In a specific aspect, a multivalent mixture of bacterial delivery vehicles, for example phagemid particles, is provided that contains identical nucleic acid payloads with the exception of inclusion of a unique "tracer" nucleic acid sequence designed in such a way that all the nucleic acid payloads packaged in the same capsid have the same associated tracer and nucleic acid payloads packaged in distinct capsids have a distinct different associated tracer. The use of such tracers allows one to detect the presence and/or the relative abundance of each bacterial delivery vehicle in the multivalent mixture of delivery vehicles through cycles of amplification, and optionally sequencing. Such amplification methods include, for example, PCR, qPCR, ddPCR, LCR, FISH or NGS using primers specific for the "tracer" sequences.

In different aspects, tracer nucleic acid sequences are embedded within coding or non-coding DNA sequences, including but not limited to reporter genes (e.g., antibiotic resistance, fluorescent proteins), tags or barcodes.

DNA barcoding, first conceptually proposed in 1982 and first practically implemented in 2003, suggested that there was a single DNA locus across all species which could be used to uniquely identify each species and, through comparison and alignment, draw a more faithful taxonomy of nature than other methods (Taylor and Harris, 2012, Mol Ecol Resour. 2012 May; 12(3):377-88). An emergent science on the brink of irrelevance: a review of the past 8 years of DNA barcoding. While no single "magic bullet" barcode was found that works for all domains of life, DNA barcodes found that work exceptionally well within certain clades, such as the mitochondrial cytochrome c oxidase subunit 1 (CO1) in animals or the 16S rRNA in bacteria, have become widely adopted to empirically generate the biological taxonomy or "tree of life" and describe ecological systems (Kress et al, 2015, Trends Ecol Evol, January; 30(1):25-35; Taylor and Harris, 2012, Mol Ecol Resour. 2012 May; 12(3):377-88).

The advent of high-throughput DNA sequencing technologies in 2005 and the decreasing cost since then have led to the generalization of DNA barcoding beyond species identification: DNA barcoding is now used in various aspects of 1) genome and chromatin mapping, 2) transcriptomics/RNA-seq, 3) ribosome profiling to analyze protein translational activity, 4) protein engineering (via phage display, mRNA/ribosome display, and yeast-two-hybrid screening), 5) DNA-encoded protein libraries, 6) cell surface DNA labeling, 7) antibody-DNA conjugates, 8) DNA-encoded small molecule and cyclic peptide libraries, and even 9) nano-particle-DNA conjugates (Liszczak and Muir, 2019, Angew Chem Int Ed Engl, March 22; 58(13):4144-4162).

In a specific, non-limiting embodiment, the tracer may be designed for use in a barcoding method. The 'barcode" represents nucleic acid sequences, the presence of which correlates with the presence of its associated bacterial delivery vehicle. In such an instance, the "barcode" is embedded within the tracer, flanked on each side by sequences (constant regions FIG. 3) that may be utilized to amplify the barcode sequences (variable regions FIG. 3) for identification and/or quantification of the barcode, which in turn indicates the presence and quantity of a specific bacterial delivery vehicle within a multivalent mixture of bacterial delivery vehicles. Using such a barcoding method provides an easy convenient method for use of multiple unique tracers the presence of which correlate with the presence of a specific bacterial delivery vehicle within a mixture of bacterial delivery vehicles.

In a specific embodiment, the tracer is embedded in a nucleic acid payload within a non-coding region of the DNA. As used herein a "non-coding region of the DNA" is a region comprising sequences that do not code for a protein. Such tracers are introduced into the nucleic acid payload in such a way that nucleic acid payload having the same tracer are packaged into identical bacterial delivery vehicles. Using such tracer nucleic acid sequences, including those that contain a barcode, both the presence and the relative abundance of each different bacterial delivery vehicle in the multivalent bacterial delivery mixture can be confirmed by PCR, qPCR, ddPCR, LCR, FISH or NGS using primers specific for sequences adjacent to the barcode as well as sequences within the barcode.

When designing a tracer for use in a non-coding region of a nucleic acid payload, one or more factors may be considered for design of efficient and effective tracers. In one aspect, the tracer should minimally affect the growth of the packaging cell line for use in production of the bacterial delivery vehicles or the production of said bacterial delivery vehicles. Further, the tracer should minimally affect the growth of the targeted bacterial cell.

The tracer may be designed in such a way that enables detection and quantification of theoretically any number of bacterial delivery vehicles within a mixture of said vehicles. Such detection can be accomplished initially using common sites, i.e. constant regions, for example constant regions flanking a variable region (e.g. C1 and C2 in FIG. 2) and that serve as targets for primer binding and subsequent amplification (see FIG. 2). Accordingly, use of such common sites permits co-amplification of a number of different tracer nucleic sequences simultaneously. In an embodiment, the tracer sequence may also allow detection of each specific tracer sequences and thus the presence of its associated bacterial delivery vehicle through use of common primer site(s) and/or variable primer site(s) per construct: V1, V2, . . . , Vx, (see FIG. 2).

In preferred embodiments, the tracer may be designed to be used in conjunction with a variety of different detection methods. Such detection methods include the use of multiple amplification cycles for detection and/or quantification of the tracer thereby leading to identification and/or quantification of the two or more bacterial delivery vehicles within a multivalent mixture of bacterial delivery vehicles. Such detection methods include, for example, PCR, qPCR (dye-based/probe-based), ddPCR (dye-based/probe-based), LCR, FISH and/or NGS.

In addition, tracers to be utilized in the disclosed methods and compositions, may be designed to have limited secondary structure and optimal melting temperatures to allow for binding of the primers/probes to the tracer nucleic acid sequences when using PCR methods such as qPCR/ddPCR/LCR/FISH/NGS detection methodology.

When considering placement of the tracer within the nucleic acid payload, a position should be chosen to minimize transcriptional or translational interference with other functional elements of the nucleic acid payload. Ideally, the tracer should lack undesired restriction sites and the tracer should be designed with limited sequence homology (>20nt) with other regions of the nucleic acid payload, the packaging cell DNA, or the target bacterial host cell DNA. Such homology can act as a substrate for undesired homologous recombination events.

Figure 2:
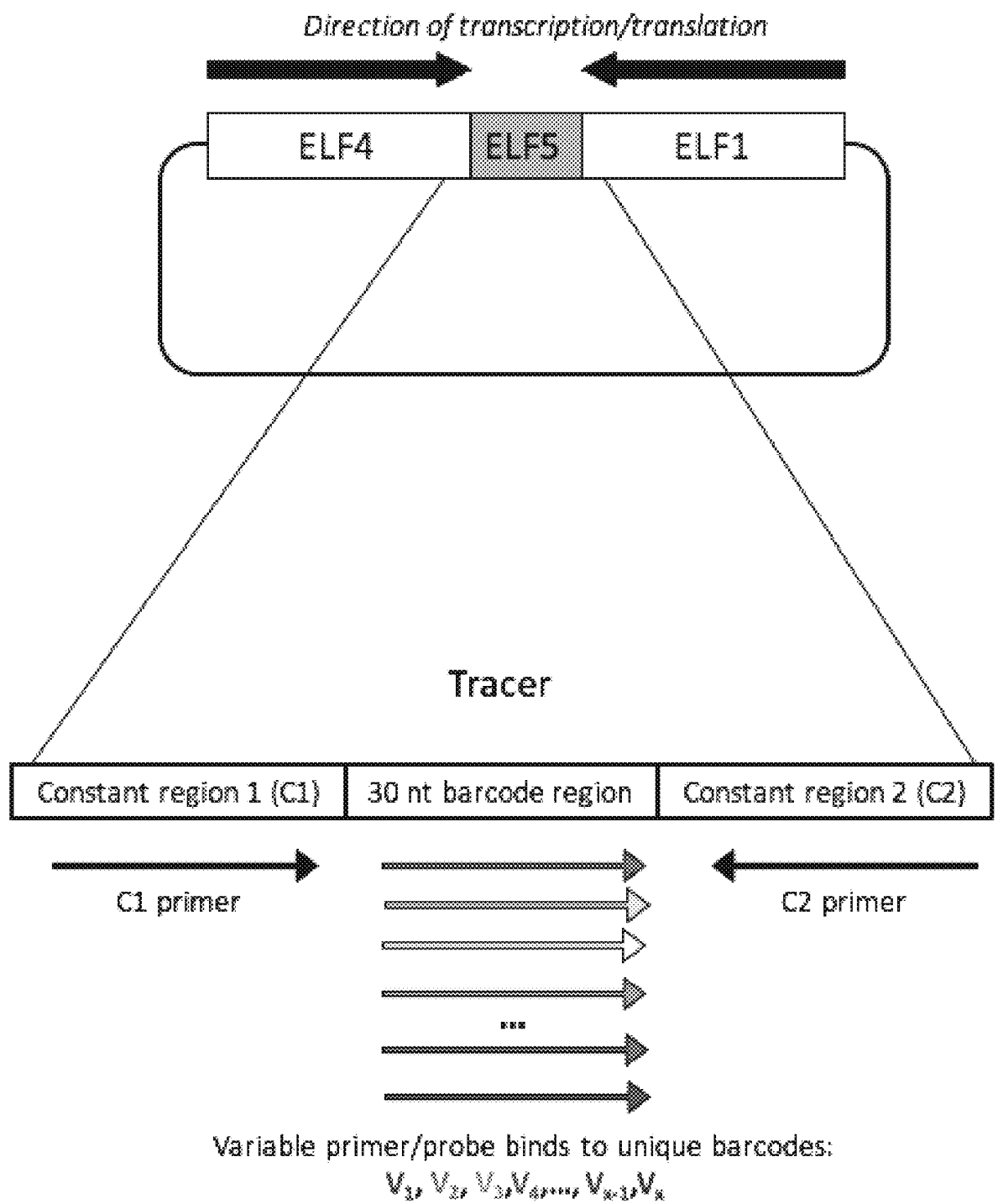
FIG. 2 depicts design and implementation of DNA tracers within non-coding DNA sequences of the DNA nucleic acid payload.

In a specific non-limiting embodiment, a DNA barcoding system may be used for identification of bacterial delivery vehicles (see, FIG. 2). The location in the DNA nucleic acid payload chosen for minimal interference with its function is the ELF5 insertion site, which is the site for the linker region of the standardized plasmid constructs. In such an embodiment, N (N=number) random nucleic acid tracers with certain structural features are generated. In preferred aspects, the length of the barcode region and constant regions may typically range in size between 25 and 50 nucleotides each. Barcode regions, as well as constant regions, should be long enough, as well as unique enough, to permit specific primer binding to allow for PCR amplification (which is a necessary step to each of the qPCR, ddPCR, and NGS methodologies) without the generation of unnecessary side amplicons. The chosen structural features, in a non-limiting example, include a tracer that is 30 nucleotides in length, where the number of barcodes generated=N where N is 1 or greater and where the GC content is limited to between about 60% to 70%. The length of the constant regions and barcodes are, in general, determined by the melting temperatures (Tms) of the desired primers to be used and depends on the detection methodology to be used. Each generated tracer nucleic acid sequence should be examined for detection of undesired restriction sites. In addition, secondary structure, melting temperatures, and sequence homology may be determined so as to minimize secondary structure, ensure a high enough melting temperature for annealing of targeting primers to the tracer sequence, while minimizing the potential for homologous recombination, respectively. Methods for testing a particular tracer for desirable structural features are well known to those of skill in the art. Once sequences are chosen, the tracer nucleic acids, which may include barcodes, are recombinantly or chemically synthesized and cloned into their respective location within the non-coding regions of the nucleic acid payloads.

TABLE 1

List of example barcodes generated.

| Barcode number | Sequence (F) | SEQ ID NO: |
|---|---|---|
| b1 | accaaacgacactcttccggcgaatcgcgc | 2 |
| b2 | agcaccccttcgccccgtcctcgtgtgtt | 3 |
| b3 | agccggaggtaggacaggtgtccgcacagg | 4 |
| b4 | cgcgatgagatggattcccgaccttccgga | 5 |
| b5 | cgctcgctgctcataatctgcgggtggcac | 6 |
| b6 | cggcacgctgtattgtccaagcgccaagca | 7 |
| b7 | ctgcggacggcggctcgcggttagcccaat | 8 |
| b8 | gatgacagcggcacacggacacaagcgtca | 22 |
| b9 | gtcccgtggatggctcgaagcctaaccgag | 23 |
| b10 | taacacggagagccatcctcagcccgtcag | 24 |
| b11 | tcctactccaccggcagccttagcgtttgg | 25 |
| b12 | tgcgcgttcttagcgtgtgagcggcctcga | 26 |

In a particular embodiment, the tracer nucleic acid sequence comprises a barcode selected from the group consisting of b1 to b12 barcodes as defined in TABLE 1.

In another aspect, the tracer nucleic acid sequence may be embedded within a coding region of the nucleic acid payload with consideration of codon usage. Of the 64 codons, three encode for stop codons and 61 encode the 20 standard amino acids. Of the 20 amino acids, only two (Met, Trp) are coded for by one unique codon, nine (Asn, Asp, Cys, Gln, Glu, His, Lys, Phe, Tyr) are coded for by two unique codons, one (Ile) is coded for by three unique codons (similarly, three unique stop codons), five (Ala, Gly, Pro, Thr, Val) are coded for by four unique codons, and three (Arg, Leu, Ser) are coded for by six unique codons. This degeneracy in 18 of the standard amino acids (in addition to stop codons) enables one to introduce codon changes into a DNA sequence such that the introduced differences in the coding sequence nevertheless encode for a protein with the identical amino acid sequence.

In one specific embodiment, a coding sequence with modified codon usage is introduced into the nucleic acid payload in such a way that all the nucleic acid payloads packaged in the same capsid have the same tracer and thus nucleic acid payloads packaged in distinct capsids have distinct tracers. In such an instance, both the presence and the relative abundance of each bacterial delivery vehicle in the multivalent mix can be confirmed by PCR, qPCR or ddPCR using primers specific for the tracer nucleic acid sequences.

For design of tracers to be embedded within protein coding regions, one or more, structural features may be considered. Such features may include those considered in the design of tracers to be inserted into non-coding regions of the nucleic acid payload. The tracer sequence to be inserted into a coding region should be designed to introduce codon changes into a protein coding region such that the introduced differences in the coding region encode for a protein with the identical amino acid sequence. The tracer should minimally affect the efficiency of protein expression or function of the protein.

In one aspect, the tracer should minimally affect the growth of the packaging bacterial cell used to produce the bacterial delivery vehicle as well as the growth of the targeted bacterial cell. Further, the tracer should minimally affect the production of the bacterial delivery vehicle within the packaging bacterial cell.

The tracer, for insertion into a coding region, may be designed in such a way that enables detection and quantification of theoretically any number of bacterial delivery vehicles within a mixture of said vehicles. Such detection can be accomplished initially using common sites, i.e. constant region, for example C1 and C2 of FIG. 3, that serve as targets for primer binding and subsequent amplification (see FIG. 3). Accordingly, use of such common sites permits co-amplification of a number of different tracer nucleic sequences. In an embodiment, the nucleic acid tracer sequence may also allow detection of each specific tracer nucleic acid sequence and thus the presence of its cognate bacterial delivery vehicle through use of one common site and one variable site per construct: V1, V2, . . . , Vx, (see FIG. 3). Such variable sites may be utilized in initial single amplification cycles, or alternatively may be used in second round amplification cycles following the use of common sites for amplification.

Each generated tracer, for insertion into a coding region, may be examined for detection of undesired restriction sites. In addition, secondary structure, melting temperatures, and sequence homology may be assessed to minimize secondary structure, ensure a high enough melting temperature for annealing of targeting primers to the tracer sequence, while minimizing the potential for homologous recombination, respectively. Once tracer sequences are chosen, the tracer nucleic acids, which may include barcodes, may be recombinantly or chemically synthesized and cloned into their respective location within the non-coding regions of the DNA nucleic acid payloads.

In a specific non-limiting embodiment, a tracer system has been developed as follows. A tracer sequence was chosen to be inserted inside the coding DNA sequence (CDS) for the TEM-1 beta-lactamase (bla) protein, which is commonly used to confer ampicillin resistance when expressed within a cell. For design of the tracer, a coding region was chosen (X) 10 codons in length from nucleotide 118 to 147 in the bla CDS. The tracer sequence included gca-cga-gtg-ggt-tac-atc-gaa-ctg-gat-ctc (SEQ ID NO: 18); which codes for the 10 amino acids, at positions 40 to 49, ARVGYIELDL (SEQ ID NO: 19). Within a chosen coding region (X) codons encoding for (X) amino acids (or stop codons), methionine (M, Met) and Tryptophan (W, Trp) amino acids are left unchanged because these amino acids have one and only one unique codon. In the bla example, none of the amino acids within the 10 amino acid segment chosen is M or W, meaning all have the amino acids have multiple codons, which can encode for each respective amino acid. Of the remaining codons/amino acids within the region X, a register is made for each amino acid such that the entirety of the codons which encode for said amino acid is numbered and listed (as one example, Ala40: 1) GCT, 2) GCC, 3) GCA, 4) GCG, seen in FIG. 3) All of the combinations among each codon possibility at each of the amino acid positions within region X are then determined and listed as unique strings within an exhaustive overall list of all possible codon combinations. As an example, for the 10 amino acid region AA40-49 in the TEM-1 beta-lactamase, one possibility, in a numerical form corresponding to amino acid position 40-49, and the specific number representing each of the specific possible codons, would be {1,1,1,1,1, 1,1,1,1,1}, another would be {2,1,1,1,1,1,1,1,1,1}, another being {3,1,1, 1,1,1,1,1,1,1}, etc, representing each of the possible codons for each amino acid position, to the exhaustion of the possible unique combinations. The three above example representations would correspond to three, thirty nucleotide sequences in which only the first codon (either GCT/GCC/GCA, 1/2/3, corresponding to position AA40, Ala) would differ, whereas the subsequent 27 nucleotides would be the first possibility at each of the remaining amino acids (so, CGT/GTT/GGT/TAT/ATT/GAA/CTT/GAT/CTT (SEQ ID NO: 20) using the ordering in FIG. 4, to represent the remaining RVGYIELDL (SEQ ID NO: 21). The exhaustive overall list of all possible codon combinations (or, sometimes, just a subset to decrease computation time) is then taken and Hamming distances are calculated between each. In the TEM-1 beta-lactamase example, each of the 10 amino acids have multiple possible codons (A=4, R=6, V=4, G=4, Y=2, 1=3, E=2, L=6, D=2, L=6) and, given these, the total number of codons which can be generated is the product 4*6*4*4*2*3*2*6*2*6, or 331,776.

Once designed, 50 bp upstream and 50 bp downstream of the 30 bp barcode, as well as the barcode, is examined for the presence of undesirable restriction sites. Only those tracers that lack such restriction sites are selected for use. Additionally, the presence of any secondary structure, melting temperatures, and sequence homology is examined to minimize secondary structure, ensure a high enough melting temperature for barcode-targeting primers, and minimize potential for homologous recombination, respectively.

The number of unique codon combinations are chosen to correspond to the number of unique members of the bacterial delivery vehicle mixtures such that maximum Hamming distances (Mohammadi-Kambs M. et al, 2017, ACS Omega. 2017 Apr. 30; 2(4): 1302-1308) between each are selected/preferred (as to both allow unique identification of each member as well as attempt to minimize the possibility of cross-reactivity/detection among/between the unique members and the unique probes/primers for each) The chosen DNA barcodes are then recombinantly or chemically synthesized and cloned into their respective location within the CDS of the DNA nucleic acid payloads.

In yet another aspect, the tracer nucleic acid sequence may be embedded in a 5' or 3' untranslated region (UTR) DNA sequence. 5' and 3' UTRs are regions on each side of a protein coding sequence (the 5' and 3' ends, respectively) that are transcribed into mRNA but not translated into a protein. In prokaryotic cells, the 5' UTR is usually much shorter (3-10 nucleotides long) than 3' UTRs and have more of an effect on protein expression than 3' UTRs. The design features of tracers for embedding in a 5' or 3' untranslated region are similar to those used for tracers to be embedded in non-coding regions of the nucleic acid payload.

Methods are provided for detecting and quantitating bacterial delivery vehicles in a multivalent bacterial delivery vehicle mixture wherein each bacterial delivery vehicle within the mixture comprises a nucleic acid payload with a unique tracer said method comprising the step of detecting and quantitating in total or each of the bacterial delivery vehicles within the mixture through performance of cycles of amplification using primers that bind to sequences within the tracer sequences. As explained above, depending on the use of primers targeting constant and/or variable regions of the tracer, all bacterial delivery vehicles or only a part thereof can be detected and/or quantified. This method thus allows detecting and/or quantifying each population of bacterial delivery vehicles comprised in the multivalent mixture and/or all bacterial delivery vehicles comprised in said mixture. Such a mixture of bacterial delivery vehicles comprising a tracer sequence embedded within their nucleic acid payload allows one to characterize a final drug product by detecting and quantitating each of the bacterial delivery vehicles within a multivalent bacterial delivery vehicle mixture. Such methods also permit identification and tracking of bacterial delivery vehicles following administration to an organism, human and/or the animal model during safety and efficacy clinical studies (shedding, biodistribution). For example, if the presence of a particular tracer sequence is found to be associated with unwanted safety and/or biodistribution profile results, its cognate bacterial delivery vehicle can be removed from the bacterial delivery vehicle mixture, rendering the final drug product safer.

Quick high throughput screening methods for testing the activity of bacterial delivery vehicles on collections of individual bacterial strains or a mixture of bacterial strains are also provided. Such screening methods provide an efficient means for identification of desirable bacterial delivery vehicles, which are capable of transferring their nucleic acid payload into a specific target bacterial cell in an efficient manner.

Additionally, methods are provided for characterizing the ability and extent of serial bacterial delivery following administrations of different vehicles on a temporal dimension (via initial transduction with delivery vehicle 1, then allowing a certain amount of time to pass, then subsequent transduction with delivery vehicle 2).

Further additional methods are provided for characterizing off-species targeting by specific bacterial delivery vehicles from the mixture when administered to a complex microbial community such as, but not limited to, human microbiota samples, of two or more prokaryotic populations.

Additionally, methods are provided for detecting and tracking bacterial delivery vehicles after administration to an organism of multivalent mixture of bacterial delivery vehicles wherein each bacterial delivery vehicle comprises a nucleic acid payload with a unique tracer, said method comprising the step of detecting and quantitating each of the bacterial delivery vehicles within the mixture through performance of cycles of amplification and optionally sequencing using primers that bind to sequences within the tracer. Such amplification methods include, for example, PCR, qPCR, ddPCR or NGS.

EXAMPLES

Example 1

Plasmid pAK272B (SEQ ID NO: 1) was modified to include a single barcode among 7 different barcodes (SEQ ID NO: 2 to 8; termed B1, B2, B3 B4, B5, B6 and B7 in FIG. 5), yielding up to 7 distinguishable plasmid variants, termed pB1, pB2, pB3, pB4, pB5, pB6 and pB7. Based on absorbance at 260 nm, DNA concentration was estimated for each plasmid variant, and used to create an equimolar mixture, aiming to have 1250 copies of each plasmid variant per microliter of mixture. The absolute number of copies of each variant in the mixture was then experimentally confirmed by droplet digital PCR (ddPCR). To achieve this, a 20-microliter ddPCR reaction was designed with 100 nM of a primer that binds to a common region of the pAK272B plasmid backbone (SEQ ID NO: 9; termed C1 in FIG. 5), 100 nM of another primer that binds specifically to a single, chosen barcode (SEQ ID NO: 10 to 16; termed V1, V2, V3, V4, V5, V6 and V7 in FIG. 5), 8 microliters of the barcoded plasmids mixture (ie, about 500 copies of each variant per microliter of final ddPCR reaction), as well as a commercially available ddPCR mastermix containing a polymerase enzyme, dNTPs and a DNA dye (QX200 ddPCR EvaGreen Supermix). One reaction was set up for each primer pair specific to an individual barcode, for a total of 7 reactions, plus 7 negative controls where the plasmid mixture was replaced by water. The ddPCR workflow was carried out as recommended by the manufacturer. As shown in FIG. 6, the number of each barcoded plasmid variant was measured well within the expected order of magnitude (227 copies per microliter, with about 500 copies per microliter expected, ie a 0.3 $\log_{10}$ difference); that small difference is likely due to the absorbance method used to estimate the initial DNA concentration. Regardless of this, the copy numbers were found similar for all 7 plasmid variants, as initially intended.

Example 2

Figure 7:
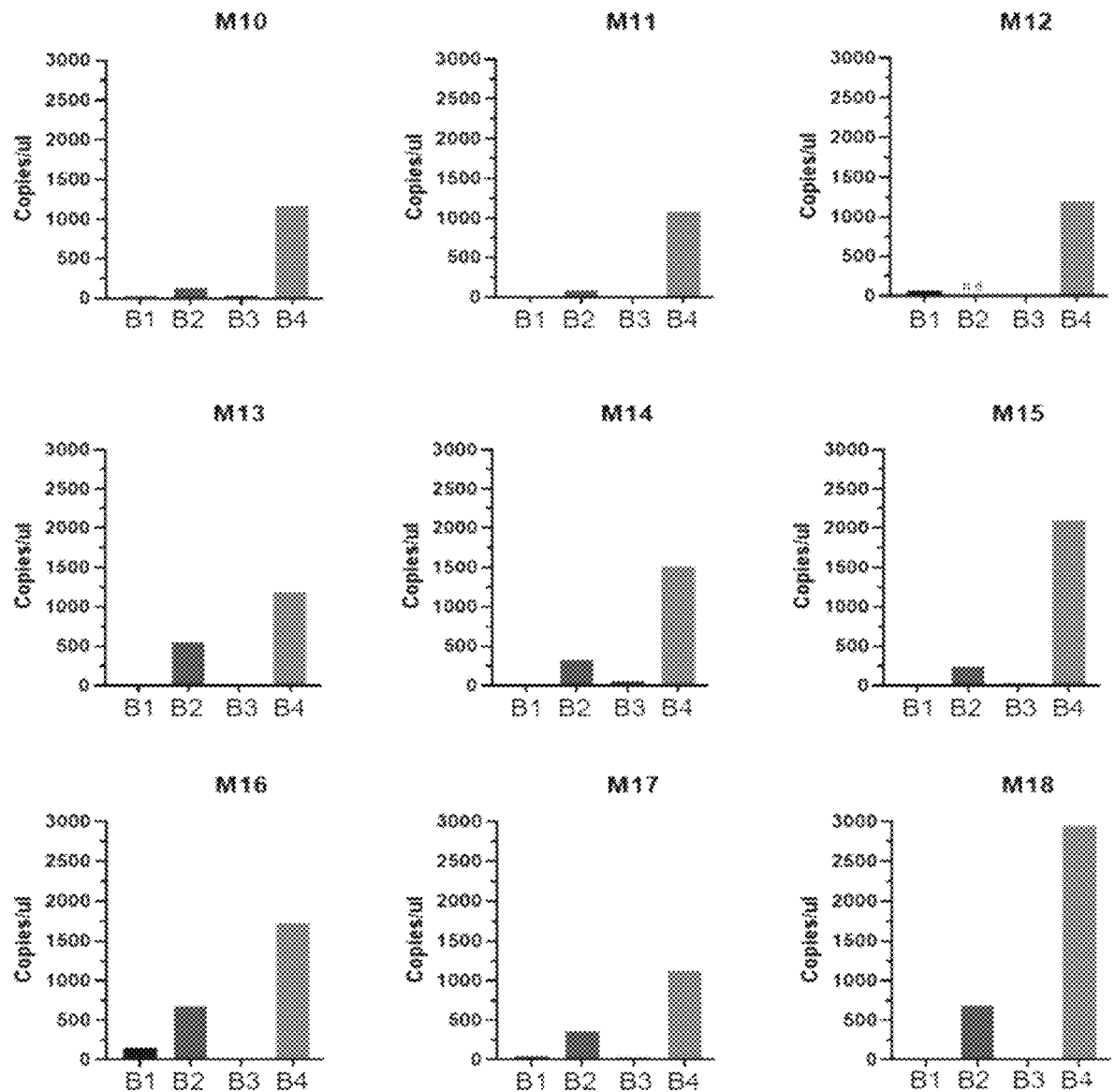
FIG. 7 represents number of each plasmid copies detected from the plasmid mixture extracted from in-vivo transduced bacteria.

Four different barcoded versions of plasmid pAK272B were used to identify differences in in vivo delivery rate into target bacteria between variants of 4 Lambda phage-derived scaffolds. The barcoded plasmids were each packaged into one Lambda phage-derived scaffold variant, and a mixture of all 4 resulting packaged phagemids was obtained by mixing $2 \times 10^7$ particles per microliter of each. One hundred microliter of this mixture was administered to 9 mice colonized with the target strain MG-GFP, and bacteria successfully transduced were recovered from the feces of the mice, by plating 4 µl of 10-fold serial dilutions of resuspended stool (pure to $10^{-5}$) for each animal on selective medium containing chloramphenicol (the plasmid pAK272B carries a chloramphenicol resistance gene). The entire transduced bacterial population contained within the 4-µl patch of pure stool sample was then grown in vitro in presence of chloramphenicol, and all plasmids present were purified by routine plasmid mini-preparation techniques. Absorbance at 260 nm was used to estimate total DNA concentration, and a reasonable amount of DNA was subjected to ddPCR; that amount was calculated to aim for no more than 80,000 copies per reaction, assuming all the DNA purified and detected corresponds to barcoded plasmids. One reaction was set up with the primer pair specific to each barcode, yielding a total of 4 reactions per original mouse sample. FIG. 7 shows the absolute number of each barcoded plasmid recovered from transduced bacteria, for each mouse of the experiment (M10 to M18). The clear abundance of barcode B4 for all 9 animals suggests that the Lambda phage-derived scaffold variant packaged with that specific plasmid variant was the most effective at delivering into the target bacteria in vivo. Other plasmid variants were also detected, but at lower copy numbers, indicating that the corresponding Lambda phage-derived scaffold delivered at lower efficacies in vivo.

What is claimed:

1. A multivalent mixture of bacterial delivery vehicles comprising at least two different bacterial delivery vehicles,
   wherein each bacterial delivery vehicle comprises a nucleic acid payload having an embedded unique tracer, wherein each different bacterial delivery vehicle possesses at least one structural feature that distinguishes it from other bacterial delivery vehicles within the mixture, and
   wherein each bacterial delivery vehicle comprises a nucleic acid payload with an identical sequence with the exception of the tracer.

2. The multivalent mixture of bacterial delivery vehicles of claim 1, wherein each bacterial delivery vehicle comprises a nucleic acid payload with a different sequence and a different tracer associated with each different payload.

3. The multivalent mixture of bacterial delivery vehicles of claim 1, wherein the tracer comprises no more than 20 nucleotides homology stretch with the DNA of the bacterial production strain and/or the DNA of the target bacterial cell.

4. The multivalent mixture of bacterial delivery vehicles of claim 1, wherein the tracer is selected from one or more of the groups consisting of:
   (i) a tracer comprising a barcode;
   (ii) a tracer comprising a constant region and a barcode;
   (iii) tracer comprising a barcode flanked on each side by a constant region;
   (iv) a tracer containing a barcode wherein the barcode is between 25 and 50 nucleic acids long;
   (v) a tracer containing a constant region wherein the constant region is between 25 and 50 nucleic acids long;
   (vi) a tracer embedded in a non-coding region;
   (vii) a tracer embedded in a coding region; and
   (viii) a tracer embedded in a coding region wherein the tracer comprises altered codon usage while encoding a protein with an unaltered amino acid sequence.

5. The multivalent mixture of bacterial delivery vehicles of claim 1, wherein the bacterial delivery vehicles are bacteriophage derived scaffolds.

6. A method for detecting and/or quantitating the bacterial delivery vehicles of claim 1, in a multivalent bacterial delivery vehicle mixture, the method comprising detecting and/or quantitating (i) each bacterial delivery vehicle and/or (ii) in total the bacterial delivery vehicles, through amplification of the tracer using primers that bind to the unique tracer sequence.

7. The method of claim 6, wherein the unique tracer has a constant region to which primers can bind for initiation of an amplification reaction, and the method comprises detecting and quantitating each bacterial delivery vehicle through amplification of the tracer using primers that bind within the constant region of the tracer sequence.

8. The method of claim 7, wherein the unique tracer further comprises variable sequences to which primers can bind for amplification and wherein said method further comprises a distinct amplification reaction or a second amplification reaction which uses primer binding to the variable sequences for an amplification method.

9. The method of claim 6, wherein the unique tracer comprises a variable region to which primers can bind for amplification, and the method comprises detecting and/or quantitating each bacterial delivery vehicle through amplification of the tracer using primers that bind within the variable region of the tracer sequence.

10. The method of claim 6, wherein each bacterial delivery vehicle comprises a nucleic acid payload with an identical sequence with the exception of the tracer.

11. The method of claim 6, wherein each bacterial delivery vehicle comprises a nucleic acid payload with different sequence and a different tracer associated with each different payload.

12. The method of claim 6, wherein the tracer comprises no more than 20 nucleotides homology stretch with the DNA of the bacterial production strain and/or the DNA of the target bacterial cell.

13. The method of claim 6, wherein the tracer is selected from one or more of the groups consisting of:
   (i) a tracer comprising a barcode;
   (ii) a tracer comprising a constant region and a barcode:
   (iii) tracer comprising a barcode flanked on each side by a constant region
   (iv) a tracer containing a barcode wherein the barcode is between 25 and 50 nucleic acids long;
   (v) a tracer containing a constant region wherein the constant region is between 25 and 50 nucleic acids long;
   (vi) a tracer embedded in a non-coding region;
   (vii) a tracer embedded in a coding region; and
   (viii) a tracer embedded in a coding region wherein the tracer comprises altered codon usage while encoding a protein with an unaltered amino acid sequence.

14. The method of claim 6, wherein detection and/or quantitation of each bacterial delivery vehicle are attained through performance of multiple cycles of amplification using primers that bind to the unique tracer nucleic acid sequence.

15. A method for detecting and/or quantitating the bacterial delivery vehicles of claim 1 in a sample derived from a subject after administration to the subject of a multivalent bacterial delivery vehicle mixture, the method comprising detecting and/or quantitating (i) each bacterial delivery vehicle and/or (ii) in total the bacterial delivery vehicles, in said sample, through performance of multiple cycles of amplification using primers that bind to the unique tracer sequence.

16. The method of claim 15, wherein the unique tracer has a constant region to which primers can bind for initiation of an amplification reaction, and the method comprises detecting and/or quantitating each bacterial delivery vehicle through amplification of the tracer using primers that bind within the constant region of the tracer sequence.

17. The method of claim 16, wherein the unique tracer further comprises variable sequences to which primers can bind for amplification and wherein said method further comprises a distinct amplification reaction or a second amplification reaction which uses primer binding to the variable sequences for an amplification method.

18. The method of claim 15, wherein the unique tracer comprises a variable region to which primers can bind for amplification, and the method comprises detecting and/or quantitating each bacterial delivery vehicle through amplification of the tracer using primers that bind within the variable region of the tracer sequence.

19. The method of claim 15, wherein each bacterial delivery vehicle comprises a nucleic acid payload with an identical sequence with the exception of the tracer.

20. The method of claim 15, wherein each bacterial delivery vehicle comprises a nucleic acid payload with different sequence and a different tracer associated with each different payload.

21. The method of claim 15, wherein the tracer comprises no more than 20 nucleotides homology stretch with the DNA of the bacterial production strain and/or the DNA of the target bacterial cell.

22. The method of claim 15, wherein the tracer is selected from one or more of the groups consisting of:
   (i) a tracer comprising a barcode;
   (ii) a tracer comprising a constant region and a barcode:
   (iii) tracer comprising a barcode flanked on each side by a constant region
   (iv) a tracer containing a barcode wherein the barcode is between 25 and 50 nucleic acids long;
   (v) a tracer containing a constant region wherein the constant region is between 25 and 50 nucleic acids long;
   (vi) a tracer embedded in a non-coding region;
   (vii) a tracer embedded in a coding region; and
   (viii) a tracer embedded in a coding region wherein the tracer comprises altered codon usage while encoding a protein with an unaltered amino acid sequence.

23. The method of claim 15, wherein detection and/or quantitation of each bacterial delivery vehicle are attained through performance of multiple cycles of amplification using primers that bind to the unique tracer nucleic acid sequence.

24. A pharmaceutical composition comprising the multivalent mixture of bacterial delivery vehicles of claim 1.

25. The pharmaceutical composition of claim 24, wherein each bacterial delivery vehicle comprises a nucleic acid payload with a different sequence and a different tracer associated with each different payload.

* * * * *

SEQUENCE LISTING

<160> NUMBER OF SEQ ID NOS: 26

<210> SEQ ID NO 1
<211> LENGTH: 12335
<212> TYPE: DNA
<213> ORGANISM: Artificial Sequence
<220> FEATURE:
<223> OTHER INFORMATION: Synthetic: Plasmid pAK272B

<400> SEQUENCE: 1

```
ctaatctctt gcccccgccc gtaatagcct ccaagagatt gaagatagta aagggcaaga      60
gctgattcgg cgttgaagga tagcggactt tcggtcaacc acaattcccc actcgacaaa     120
accagccgtg cgaataactc tgaaagtaca agcaacccaa gagggctgag cctaaactca     180
gctaattcct aagtgagcta aagactcgaa gtgacagctc ttaataaata gagcgggaac     240
gtcgaacggt cgtgaaagta atagtacaac gggtattaac ttactgagga tattgcttga     300
agctgtaccg tttattggg tgaacgaata agatccagca attcagccaa agaagctacc     360
aatttttagt ttaagagtgt cacgtctgac ctcgcgggta gattgccgaa cgtagagctt     420
acgagccagc ggaaacagta gccgcaggat aagtaagggg agtaagtgat cgaacgaatc     480
agaagtgaca atatacttag gctggatctc gtcccgtgaa tcccaaccct caccaactac     540
gagataagag gtaagccaaa aatcgacttg gtggcgacca cgactgttc ccccctgta      600
actaatcgtt ccgtcaaaac ctgacttact tcaaggccaa ttccaagcgc aaacaatacc     660
gtcctagttc ttcggttaag tttccgaagt aggagtgagc ctacctccgt ttgcgtcttg     720
ttaccactga cccagctatt tactttgtat tgcctgcaat cgaatttctg aactctcaga     780
tagtggggat aacgggaaag ttcctatatt tgcgaactaa cttagccgtc cacctcgaag     840
ctacctactc acacccaccc cgcgcggggt aaataaggca ctaatcccag ctgagagctg     900
gcgtagcact tagccacaag ttaattaaca gttgtctggt agtttggcgg tattaggaag     960
atcctagaag caaggcagag ttagttctaa cctaaagcca caaataagac aggttgccaa    1020
agcccgccgg aaattaaatc ttgctcagtt cggtaacgga gtttccctcc cgcgtactta    1080
attcccaata agaaacgcgc ccaagtccta tcaggcaaaa ttcagcccct tcccgtgtta    1140
gaacgagggt aaaaatacaa gccgattgaa caagggttgg gggcttcaaa tcgtcgttta    1200
ccccactttta caacggagat taagtagttc acccctatagt acgaagcaga actatttcga    1260
ggggcgtgca ataatcgaat cttctgcggt tgacttaaca cgctagggac gtgccctcga    1320
ttcaatcgaa ggtactccta ctcagactgc ctcacaccca gctagtcact gagcgataaa    1380
attgacccgc cctctaggga agcgagtacg tcccaagggg ctccggacag ggctatatag    1440
gagagtttga tctcgccccg acaactgcaa ccctcaactc ccttagataa tattgttagc    1500
cgaagttgca cgacccgccg tccacggact gctcttaggg tgtggctcct taatctgaca    1560
acgtgcaacc cctatcgaag tcgattgttt ctgcgaaagg tgttgtccta atagtcccga    1620
aatttggccc ttgtaggtgt gaaaccactt agcttcgcgc cgtagtccta aaggcccacc    1680
tattgacttt gtttcgggta gcactaggaa tcttaacaat ttgaatttgg acgtggaacg    1740
cgtacacctt aatctccgaa taattctagg gatttggaag tcctctacgt tgacacacct    1800
acactgctcg aagtaaatat acgaataacg cgggcctcgc ggagccgttc cgaatcgtca    1860
cgtgttcgtt tactgttaat tggtggcaaa taagcaatat cgtagtccgt caggcccagc    1920
cctgttatcc acggcgttat ttgtcaaatt gcgtagaact ggattgactg cctgacaata    1980
cctaattatc ggtacgaagt ccccgaatct gtcgggctat ttcactaata ctttccaaac    2040
gccccgtatc caagaagaac gaatttatcc acgctcccgt cttgggacg aataccgcta     2100
caagtggaca gaggatcggt acgggcctct aataaatcca acactctacg ccctcttcaa    2160
gagctagaag aacagggtgc agttggaaag ggaattattt cgtaaggcga gccaataccg    2220
```

```
taattaattc ggaagagtta acacgattgg aagtaggaat agtttctaac cacggttact    2280
aatcctaata acggaacgct gtctgataga ttagtgtcag cgctcggtac caaagaaaaa    2340
taaaaagacg ctgaaaagcg tcttttttatt tttcggtcca gtgtaactca ggcaaaagca   2400
cgtaatattc gtactttctt cctccgtaag cgtcacccac attccttaaa gagtgcatgt    2460
gcatattttg ttatcaataa aaaggccgc gatttgcggc cttattgttc gtcttgccgg     2520
attacgcccc gccctgccac tcatcgcagt attgttgtaa ttcattaagc attctgccga    2580
catggaagcc atcacaaacg gcatgatgaa cttggatcgc cagtggcatt aacaccttgt    2640
cgccttgcgt ataatatttt cccatagtga aaacgggggc gaagaagttg tccatatttg    2700
ctacgtttaa atcaaaactg gtgaaactca cccacggatt ggcactgacg aaaaacatat    2760
tttcgataaa ccctttaggg aaatatgcta agttttcacc gtaacacgcc acatcttgac    2820
tatatatgtg tagaaactgc cggaaatcgt cgtggtattc tgaccagagc gatgaaaacg    2880
tttcagtttg ctcatggaaa acggtgtaac aagggtgaac actatcccat atcaccagct    2940
caccgtcttt cattgccata cgaaactccg gatgtgcatt catcaggcgg gcaagaatgt    3000
gaataaaggc cggataaaac ttgtgcttat ttttctttac ggttttttaaa aaggccgtaa   3060
tatccagctg aacggtttgg ttataggtgc actgagcaac tgactggaat gcctcaaaat    3120
gttctttacg atgccattga cttatatcaa ctgtagtata tccagtgatt ttttttctcca  3180
ttttagcttc cttagcttgc gaaatctcga taactcaaaa aatagtagtg atcttatttc    3240
attatggtga aagttgtctt acgtgcaaca ttttcgcaaa aagttggcgc tttatcaaca    3300
ctgtcggaat gacaaatggt tccaattatt gaacacccct cggggtgttt ttttgtttct    3360
ggtttcccga ggccggcctg cgctagcgga gtgtatactg gcttactatg ttggcactga   3420
tgagggtgta agtgaagtgc ttcatgtggc aggagaaaaa aggctgcatc ggtgcgtcag    3480
cagaatatgt gatacaggat atattccgct tcctcgctca ctgactcgct acgctcggtc    3540
gttcgactgt ggcgagcgga aatggcttac gaacggggcg gagatttcct ggaagatgcc    3600
aggaagatac ttaacaggga agtgagaggg tcgcggcaaa gccgttttttc cataggctcc   3660
gccccctga caagcatcac gaaatctgac gctcaaatca gtggtggcga aacctgacag    3720
gactataaag ataccaggcg tttccccctg gcggctccct cgtgcgctct cctgttcctg    3780
cctttcggtt tgccggtgtc attcctctgt tacggccgag tttgtctcat tccacgcctg    3840
acactcagtt ccgggtaggc agttcgctcc aagctggact gtatgcacga accccccgtt    3900
cagtccgacc gctgcgcctt atccggtaac tatcgtcttg agtccaaccc ggaaagacat    3960
gcaaaagcac cactggcagc agccactggt aattgattta gaggagttag tcttgaagtc    4020
atgcgccgga taaggctaaa ctgaaaggac aagttttggc gactgcgctc ctccaagcca    4080
gttacctcgg ttcaaagagt tggtagctca gagaaccttc gaaaaaccgc cctgcaaggc    4140
ggtttttttcg tttcagagc aagagattac gcgcagacca aaacgatctc aagaagatca    4200
tcttattaat cagataaaat atttctagat ttcagtgcaa tttatctctt caaatgtagc    4260
accggcgcgc cgtgaccaat tattgaaggc cgctaacgcg gcctttttttt gtttctggta   4320
tcccgaatgg agcgacttct ccccaaaaag cctcgctttc agcacctgtc gtttcctttc    4380
ttttcagagg gtatttttaaa taaaaacatt aagttatgac gaagaagaac ggaaacgcct   4440
taaaccggaa aattttcata aatagcgaaa acccgcgagg tcgccgcccc gtaacctgtc    4500
ggatcaccgg aaaggacccg taagtgata atgattatca tctacatatc acaacgtgcg    4560
taaagggtaa gtatgaaggt cgtgtactcc atcgctacca aattccagaa aacagacgct    4620
```

```
ttcgagcgtc ttttttcgtt ttggtcacga cgtacggtgg aagattcgtt accaattgac   4680
agctagctca gtcctaggta tatacataca tgcttgtttg tttgtaaact actgttttca   4740
ttaaagagga gaaaggaagc catgtccatc tatcaggagt ttgttaacaa gtattccctg   4800
tctaaaaccc tgcgttttga actgatcccg cagggcaaaa ctttggaaaa cattaaagcg   4860
cgtggcctga ttctggatga cgaaaaacgt gcaaaggatt acaagaaagc taaacagatc   4920
atcgacaaat atcaccagtt ctttatcgaa gaaattctgt cgtcggtgtg catcagtgag   4980
gatctgttac agaattattc tgatgtatac tttaaactta aaagtccga tgacgataat    5040 ctgcaaaaag atttcaagtc agccaaagat accatcaaga acagatctc agaatatatt    5100 aaagatagcg aaaagttcaa aaacctgttt aaccaaaacc tcattgatgc taagaaaggc   5160
caagaatctg acctgatctt atggctgaaa cagagcaaag ataacggcat tgaactgttc   5220
aaagctaata gcgacatcac cgatattgat gaagcgctcg aaatcatcaa gtctttcaaa   5280
ggctggacga cgtatttcaa aggttttcat gaaaaccgta agaatgtata ttcgagcaac   5340
gatattccga cctctattat ttatcgtatc gtggacgaca acctgccgaa gtttctggaa   5400
aacaaagcga aatatgaatc tctgaaagac aaagcaccgg aagctattaa ctatgaacag   5460
atcaagaaag atctggcgga agaactgacc ttcgacatcg actataaaac ctccgaagtt   5520
aaccagcgtg ttttctcact ggacgaggtt ttcgaaatcg ctaatttcaa caattacctg   5580
aatcaatctg gcatcaccaa attcaacacc attattggtg gcaaatttgt taacggcgaa   5640
aacaccaagc gtaagggcat caacgaatac attaacctgt atagccaaca aatcaacgac   5700
aaaaccctga aaagtataa atgtccgtt ctgtttaaac agattttatc ggacaccgaa     5760
tctaaatcct tcgtaattga taaactggaa gatgatagcg acgttgtcac cacgatgcag   5820
agcttttatg agcagattgc ggcgttcaaa accgtggaag agaaatctat taagaaaact   5880
ctgtccctgc tctttgacga cctcaaagcg cagaaactag atctgtctaa gatttacttt   5940
aaaaacgaca aatctctgac cgatctcagt caacaagttt tcgatgacta tagcgtgatc   6000
ggcacggcag ttttggaata catcacccaa caaatcgcgc cgaaaaatct ggacaacccg   6060
tccaagaagg aacaggaact gattgcaaag aaaacagaaa aagctaaata cctgagctta   6120
gaaactatca aactggcact tgaggaattt aataaacatc gtgatattga taaacagtgt   6180
cgttttgagg aaattctggc gaactttgcg gcaatcccga tgatcttcga cgaaattgct   6240
caaaacaaag acaatctggc gcagatctct atcaagtacc agaatcaggg taagaaagat   6300
ctgcttcaag catctgcgga ggacgatgtg aaagcaatta agacttatt agatcagacg   6360 aataacttat tacacaagct caaaatcttc cacatcagcc agagcgagga caaggcgaac   6420
attctggata agatgaaca cttctatctg gtgttcgaag aatgttactt cgaactggca   6480
aacatcgtcc ctctctacaa taaaatccgc aactacatca cgcagaagcc ttactctgac   6540
gagaaattca aactgaactt cgaaaacagc acgctggcga acggctggga taagaacaaa   6600
gagccggaca acaccgcaat cctgttcatc aaagacgaca atactatct gggcgtaatg    6660 aacaagaaga caacaagat cttcgacgat aaagcgatca agaaaacaa gggtgaaggc    6720 tataagaaaa tcgtgtacaa gctcctgccg ggtgcgaata aatgttacc gaaagtgttc    6780 ttttccgcga aaagcatcaa attctacaac ccgtctgagg atattctgcg catccgcaat   6840
catagcacgc acactaaaaa cggtagcccg cagaaagggt atgaaaaatt cgaatttaat   6900
atagaggact gccgtaagtt catcgacttc tataaacaga gcatttccaa acatccggaa   6960
```

```
tggaaagact tcggcttccg tttctctgac actcagcgct ataatagcat cgacgagttc    7020
taccgcgaag tggagaatca gggctataaa ctgaccttcg agaacattag tgagtcgtac    7080
atcgactccg ttgtgaatca gggtaaactg tacctgtttc agatctataa taaagacttt    7140
agcgcgtaca gcaaaggccg tccgaatctg cacacccttt actggaaagc attatttgac    7200
gaacgtaacc tgcaagatgt ggtgtataaa ctgaacggtg aggcggaact tttctaccgt    7260
aaacagagta tcccgaagaa aatcacgcat ccggcaaaag aagctattgc caacaaaaac    7320
aaagacaacc cgaagaaaga atcagtattc gaatatgacc tgatcaaaga taaacgtttc    7380
accgaagata agttcttttt ccactgtccg attaccatca acttcaaatc tagcggtgcg    7440
aacaagttca cgatgaaat taacttatta ctgaaagaga aagctaatga cgtacacatc    7500
ttatctattg atcgcggtga acgtcattta gcatactata cactggtaga tggtaaaggt    7560
aatattatta aacaggatac tttcaatatt atcggtaatg accgtatgaa aaccaactat    7620
cacgataagc tggcggcgat cgaaaaagat cgtgattctg cgcgtaaaga ttggaagaaa    7680
attaacaata tcaaagaaat gaaagaaggc tatctgagcc aagtggtgca cgagatcgca    7740
aaactggtga ttgaatataa cgctatcgtg gttttcgaag atctgaactt tggttttaaa    7800
cgtggtcgct tcaaagtaga aaaacaggtg taccaaaaac tggaaaaaat gctgattgaa    7860
aaactgaact atctggtttt taaagacaac gaatttgaca aaacgggtgg cgtactccgt    7920
gcctatcagc tgaccgctcc gttcgaaacg ttcaagaaaa tgggtaaaca acgggattt   7980 atctattatg tgccagctgg tttcacctcc aagatttgtc cagttacggg cttcgttaac    8040
cagctgtacc cgaaatacga gagcgttagc aaatctcaag aattttttcag caaattcgac    8100 aagatctgct ataatctgga taaaggctat ttcgagttca gcttcgatta caaaaacttc    8160
ggcgataaag cggctaaagg taagtggact attgctagct ttggtagccg tctgattaac    8220
tttcgcaact ccgacaaaaa ccataattgg gacacgcgtg aagtgtatcc gaccaaagaa    8280
ctggaaaaat tactgaaaga ctattccatc gaatatggtc atggggagtg cattaaagcg    8340
gcgatttgcg gtgaatccga taagaaattt ttcgccaaac tgaccagcgt gcttaacacc    8400
attctgcaaa tgcgtaattc taaaacgggt acggagctgg actacctgat ttctccggta    8460
gccgacgtta acggcaactt cttcgattct cgtcaagcac cgaaaaatat gccacaagac    8520
gcggatgcca acggtgcata ccatatcggc ttaaaaggct taatgttatt aggccgtatc    8580
aagaataatc aggagggcaa gaaattaaat ctggttatca aaaacgaaga atacttcgag    8640
ttcgttcaga atcgtaacaa ttaatgtatg cttaagcagc tcggtaccaa agacgaacaa    8700
taagacgctg aaaagcgtct ttttttcgttt tggtcctgtt gcggcgcgat agtgtgaaca    8760
tgctatagac ttctggtgct acccgactga caattaatca tccggctcgt ataatgctag    8820
caatttctac tgttgtagat catgacaacg gacagcagtt atacgtctaa gaactttaaa    8880
taatttctac tgttgtagat tcgagacgaa caataaggcc tccctaacgg ggggcctttt    8940
ttattgataa caaaagtaac ttcgagcttg tctacctcct agcaccatta ttgcaattaa    9000
taaacaacta acggacaatt ctacctaaca gttttcatat atgacgagca gttaagtgat    9060
gagtaaaggt gaggaattat ttactggtgt gttccgatc ttagttgaac tggacggcga    9120
tgttaacggt cataaattca gtgttcgtgg tgaaggtgaa ggtgatgcaa ccaacggtaa    9180
gctgaccctg aaattcatct gcactactgg aaaattacca gtaccgtggc ctactctggt    9240 gactacccctg acctatggtg ttcagtgttt ttctcgttac cctgaccaca tgaagcaaca    9300
tgatttcttc aaatctgcaa tgccggaagg ttatgtacag gagcgcacca tttctttcaa    9360
```

```
agacgatggc acgtataaaa cccgtgcaga ggttaaattt gaaggtgaca ctctggtgaa   9420
tcgtattgaa ctgaaaggca ttgatttcaa agaggacggc aatatttag gccacaaact    9480
ggaatataac ttcaactccc ataacgttta catcaccgca gacaaacaga agaacggtat    9540
caaagctaac ttcaaaattc gccataacgt tgaagatggt agcgtacagc tggcggatca    9600
ttaccaacag aacactccga ttggagatgc tcctgtttta ctgccggata accactacct    9660
gtccacccag tctaaactgt cgaaggatcc gaacgaaaag cgcgaccaca tggtgttatt    9720
agagttcgtt accgctagtg gtatcacgca cggtatggat gaactctaca ataagacga    9780
acaataaggg gagcgggaaa ccgctcccct tttttattga taacaaaagt aaattgcacg    9840
ctgatagtct cccaattgcg aaggaccaaa acgaaaaaac acccttcgg gtgtcttttc     9900
tggaattgg taccgagtac taggtatcgt gtaagtagcg aaggcccgta cgcgagataa     9960
actgctaggc aaccgcgact ctacgactgg tgctcgattt aatttcgctg acgtaaagaa   10020
attatcggca gtgcgtcaac tgccgtatct ttatcttaat taggtagttg acaagccct    10080
tgaaagaaat agcaagagcc tgcctctcta ttgaagtcac ggcgaaagtc gggtagaaat   10140
caaagaaagc agaaattaaa tcggagtaac actaaggtgg ataactccg taactgacta    10200
cgcctttctc tagactttac ttgaccagat acactgtctt tgacacgttg aaggattaga   10260
gcaatcaaat ccaagactgg ctaagcacga agcaactctt gagtgttaaa aagttatctc   10320
ctgtattcgg gaagcgggta ctagaagatt gcagggactc cgacgttaag taaattacaa   10380
agtaataagt atcgttcagg atcacgttac cgcaataaga agcgagaata atataatttc   10440
cgaagtgctt acccagtag tgactattcc tataaccctt ctgagtgtcc ggaggcggaa    10500
atttgccacg aaagagaaag tatttccccg acaataataa aggggcgctc ctcagctttt   10560
ccacttggtt gggtaagcta ggcaactctg aaaggagttt cggcgaattg aagccgacag   10620
ctttgaattg ttttaggggc gttattcgag ggcaatcgga gctaacttca agactacttc   10680
tttgttgaat actaaatagt gcaaaggtcg tgtttcctca aggatactcc gctaacaata   10740
taggattcca atcagattca gcactggcgg tacgggtgtt gcggtgaggc gttcgggttt   10800
acggctcgaa gctagcacgg taggaagcct gacaatcacc aagcaaaagg gccgtcgaag   10860
gcccacaaga tacgaaagct ctcgaagcct tatccttgac cgatccacct atttaggcag   10920
ttacgcacaa aagctaccca ataatccgtg acaggcacaa tatcacgaa caaaaccgaa     10980
aactctcgta cacggttagg ttttcgctag gaagaataaa cctctatctt gattataaga   11040
aggctcccca agcacccca aaaccgaaat agcggtttgc aataagggac aagttacgag    11100
tgtagacacg cagaattatc cagcctttag tctttaggaa ggcaaagcta ttgtacgcgg   11160
tagccgtcgt agcaatttac caactgtaga attattggac acacgtagga agggcttaca   11220
gttgaagttt aataaggtca cacgcaaaac cgctaaggaa taatcgcacc gttagcgaaa   11280
gaatatttca gagcggttag taaaggttga gtaaagtgag attccaaagt gagccttat    11340
aaaaagtaaa gagctataat aaaaccgtcg agcagaaaac aatcgcctga atctcaagc    11400
acgttgccct ttctaacgtc gctaaggttt cgtaaacccg tttgattagg aagaagaata   11460
agtaacccga ttaggttga gatcgcgggt tatcggtttg gattaaaagt ggataccagc    11520
ggagtcaacg ccgacgcaaa cgtacagtga tccaatcctg ttgcacggtc aagcacaatc   11580
agctcgcaag atcttggaat agtgtgccca acagtttagt tgagggccac gttccgacta   11640
caagttgctt caagagggga atttggattt ggcaatagcc ccccgtttct acctcaagag    11700
```

-continued

```
gcgacgagta ttaaccgcgc cagctgtcgg cacaagggcc aaagaagatt ccaatttctt    11760
attcccgaat aacctccgaa tccctgcggg aaaatcaccg accgaatagc ctagaagcaa    11820
gggggaacag ataggtataa ttagcttaag agagtaccag ccgtgacaac agcgtagtaa    11880
ccacaaactt acgctggggc ttctttggcg gattttttaca gatactaaca aggtgatttg    11940
aagtacctta gttgaggatt taaacgcgct atccggtaat ctccaaattg ggaaataccg    12000
ttcaaagagg gctagaatta cttaaaagcc ttcacaccgc ctgcgctata cgcgcccact    12060
ctcccgttta tccgtccaag cggaagcagg gcgatcctcc gctaagatat tcttacgtgt    12120
aacgtagcta agtatcccaa atagctggcg tacgcgttga acaccgccta gaggatcgtg    12180
actcgccgga cgagcgtgtt attggggact tacgccagcg tagactacaa cgcgcccaga    12240
ttaaccctgc acgtattgcc ttgaataacg tactaatctc tccggctctc gacaatctat    12300
cgagcgactc gattatcaac gggtgtcttg cagtt                               12335
```

<210> SEQ ID NO 2
<211> LENGTH: 30
<212> TYPE: DNA
<213> ORGANISM: Artificial Sequence
<220> FEATURE:
<223> OTHER INFORMATION: Synthetic: Barcode B1

<400> SEQUENCE: 2
accaaacgac actcttccgg cgaatcgcgc                                        30

<210> SEQ ID NO 3
<211> LENGTH: 30
<212> TYPE: DNA
<213> ORGANISM: Artificial Sequence
<220> FEATURE:
<223> OTHER INFORMATION: Synthetic: Barcode B2

<400> SEQUENCE: 3 agcaccccctt cgcccccgtc ctcgtgtgtt                                       30

<210> SEQ ID NO 4
<211> LENGTH: 30
<212> TYPE: DNA
<213> ORGANISM: Artificial Sequence
<220> FEATURE:
<223> OTHER INFORMATION: Synthetic: Barcode B3

<400> SEQUENCE: 4
agccggaggt aggacaggtg tccgcacagg                                        30

<210> SEQ ID NO 5
<211> LENGTH: 30
<212> TYPE: DNA
<213> ORGANISM: Artificial Sequence
<220> FEATURE:
<223> OTHER INFORMATION: Synthetic: Barcode B4

<400> SEQUENCE: 5
cgcgatgaga tggattcccg accttccgga                                        30

<210> SEQ ID NO 6
<211> LENGTH: 30
<212> TYPE: DNA
<213> ORGANISM: Artificial Sequence
<220> FEATURE:
<223> OTHER INFORMATION: Synthetic: Barcode B5

<400> SEQUENCE: 6
cgctcgctgc tcataatctg cgggtggcac                              30

<210> SEQ ID NO 7
<211> LENGTH: 30
<212> TYPE: DNA
<213> ORGANISM: Artificial Sequence
<220> FEATURE:
<223> OTHER INFORMATION: Synthetic:  Barcode B6

<400> SEQUENCE: 7
cggcacgctg tattgtccaa gcgccaagca                              30

<210> SEQ ID NO 8
<211> LENGTH: 30
<212> TYPE: DNA
<213> ORGANISM: Artificial Sequence
<220> FEATURE:
<223> OTHER INFORMATION: Synthetic:  Barcode B7

<400> SEQUENCE: 8
ctgcggacgg cggctcgcgg ttagcccaat                              30

<210> SEQ ID NO 9
<211> LENGTH: 41
<212> TYPE: DNA
<213> ORGANISM: Artificial Sequence
<220> FEATURE:
<223> OTHER INFORMATION: Synthetic:  primer that binds to a common
      region of the pAK272B plasmid backbone

<400> SEQUENCE: 9
acggaacgct gtctgataga ttagtgtcag cgctcggtac c                 41

<210> SEQ ID NO 10
<211> LENGTH: 41
<212> TYPE: DNA
<213> ORGANISM: Artificial Sequence
<220> FEATURE:
<223> OTHER INFORMATION: Synthetic:  primer that binds specifically to
      B1

<400> SEQUENCE: 10
tgcacatgca ctctttaagg aatgtgggtg acgcttacgg a                 41

<210> SEQ ID NO 11
<211> LENGTH: 30
<212> TYPE: DNA
<213> ORGANISM: Artificial Sequence
<220> FEATURE:
<223> OTHER INFORMATION: Synthetic:  primer that binds specifically to
      B2

<400> SEQUENCE: 11
aacacacgag gacgggggcg aaggggtgct                              30

<210> SEQ ID NO 12
<211> LENGTH: 30
<212> TYPE: DNA
<213> ORGANISM: Artificial Sequence
<220> FEATURE:
<223> OTHER INFORMATION: Synthetic:  primer that binds specifically to
      B3

```
<400> SEQUENCE: 12
cctgtgcgga cacctgtcct acctccggct                                              30

<210> SEQ ID NO 13
<211> LENGTH: 30
<212> TYPE: DNA
<213> ORGANISM: Artificial Sequence
<220> FEATURE:
<223> OTHER INFORMATION: Synthetic:  primer that binds specifically to
      B4

<400> SEQUENCE: 13
tccggaaggt cgggaatcca tctcatcgcg                                              30

<210> SEQ ID NO 14
<211> LENGTH: 30
<212> TYPE: DNA
<213> ORGANISM: Artificial Sequence
<220> FEATURE:
<223> OTHER INFORMATION: Synthetic:  primer that binds specifically to
      B5

<400> SEQUENCE: 14
gtgccacccg cagattatga gcagcgagcg                                              30

<210> SEQ ID NO 15
<211> LENGTH: 30
<212> TYPE: DNA
<213> ORGANISM: Artificial Sequence
<220> FEATURE:
<223> OTHER INFORMATION: Synthetic:  primer that binds specifically to
      B6

<400> SEQUENCE: 15
tgcttggcgc ttggacaata cagcgtgccg                                              30

<210> SEQ ID NO 16
<211> LENGTH: 30
<212> TYPE: DNA
<213> ORGANISM: Artificial Sequence
<220> FEATURE:
<223> OTHER INFORMATION: Synthetic:  primer that binds specifically to
      B7

<400> SEQUENCE: 16
attgggctaa ccgcgagccg ccgtccgcag                                              30

Figure 3:
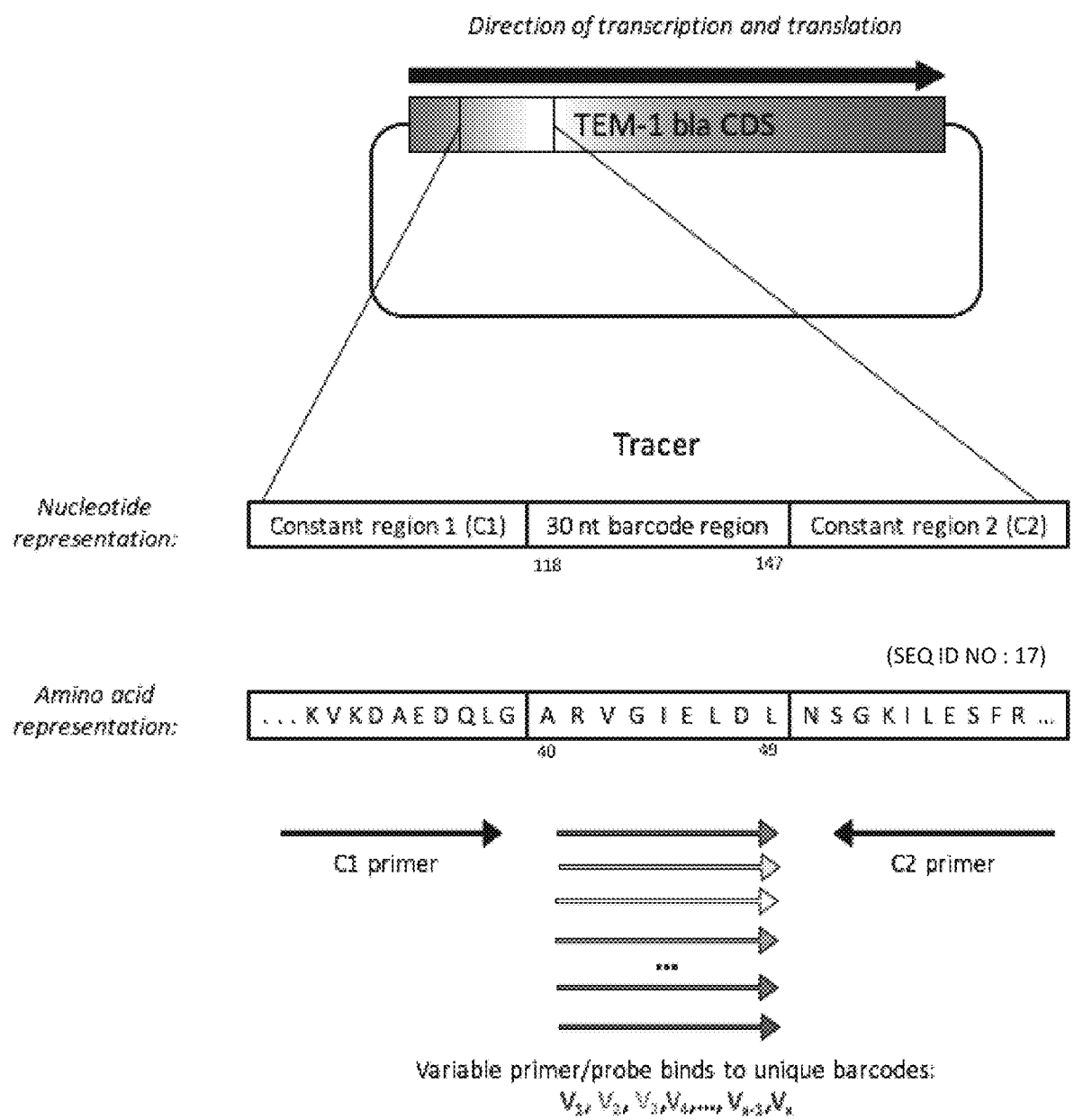
FIG. 3 depicts design and implementation of DNA within synonymous coding DNA sequences of the DNA nucleic acid payload.

<210> SEQ ID NO 17
<211> LENGTH: 29
<212> TYPE: PRT
<213> ORGANISM: Artificial Sequence
<220> FEATURE:
<223> OTHER INFORMATION: Synthetic:  Figure 3 (amino acid
      representation)

<400> SEQUENCE: 17

Lys Val Lys Asp Ala Glu Asp Gln Leu Gly Ala Arg Val Gly Ile Glu
1               5                   10                  15

Leu Asp Leu Asn Ser Gly Lys Ile Leu Glu Ser Phe Arg
            20                  25

<210> SEQ ID NO 18
<211> LENGTH: 30
<212> TYPE: DNA
<213> ORGANISM: Artificial Sequence
```

```
<220> FEATURE:
<223> OTHER INFORMATION: Synthetic: Sequence encoding ARVGYIELDL

<400> SEQUENCE: 18
gcacgagtgg gttacatcga actggatctc                                           30

<210> SEQ ID NO 19
<211> LENGTH: 10
<212> TYPE: PRT
<213> ORGANISM: Artificial Sequence
<220> FEATURE:
<223> OTHER INFORMATION: Synthetic: Sequence encoded by SEQ ID NO: 18

<400> SEQUENCE: 19

Ala Arg Val Gly Tyr Ile Glu Leu Asp Leu
1               5                   10

<210> SEQ ID NO 20
<211> LENGTH: 27
<212> TYPE: DNA
<213> ORGANISM: Artificial Sequence
<220> FEATURE:
<223> OTHER INFORMATION: Synthetic: Sequence encoding RVGYIELDL

<400> SEQUENCE: 20
cgtgttggtt atattgaact tgatctt                                              27

<210> SEQ ID NO 21
<211> LENGTH: 9
<212> TYPE: PRT
<213> ORGANISM: Artificial Sequence
<220> FEATURE:
<223> OTHER INFORMATION: Synthetic: Sequence encoded by SEQ ID NO: 20

<400> SEQUENCE: 21

Arg Val Gly Tyr Ile Glu Leu Asp Leu
1               5

<210> SEQ ID NO 22
<211> LENGTH: 30
<212> TYPE: DNA
<213> ORGANISM: Artificial Sequence
<220> FEATURE:
<223> OTHER INFORMATION: Synthetic: Barcode B8

<400> SEQUENCE: 22
gatgacagcg gcacacggac acaagcgtca                                           30

<210> SEQ ID NO 23
<211> LENGTH: 30
<212> TYPE: DNA
<213> ORGANISM: Artificial Sequence
<220> FEATURE:
<223> OTHER INFORMATION: Synthetic: Barcode B9

<400> SEQUENCE: 23
gtcccgtgga tggctcgaag cctaaccgag                                           30

<210> SEQ ID NO 24
<211> LENGTH: 30
<212> TYPE: DNA
<213> ORGANISM: Artificial Sequence
<220> FEATURE:
<223> OTHER INFORMATION: Synthetic: Barcode B10
```

```
<400> SEQUENCE: 24
taacacggag agccatcctc agcccgtcag                                    30

<210> SEQ ID NO 25
<211> LENGTH: 30
<212> TYPE: DNA
<213> ORGANISM: Artificial Sequence
<220> FEATURE:
<223> OTHER INFORMATION: Synthetic:  Barcode B11

<400> SEQUENCE: 25
tcctactcca ccggcagcct tagcgtttgg                                    30

<210> SEQ ID NO 26
<211> LENGTH: 30
<212> TYPE: DNA
<213> ORGANISM: Artificial Sequence
<220> FEATURE:
<223> OTHER INFORMATION: Synthetic:  Barcode B12

<400> SEQUENCE: 26
tgcgcgttct tagcgtgtga gcggcctcga                                    30
```